US008506908B2

(12) United States Patent
Benn et al.

(10) Patent No.: US 8,506,908 B2
(45) Date of Patent: Aug. 13, 2013

(54) ELECTROCHEMICAL DETECTION SYSTEM

(75) Inventors: Jim Benn, Arlington, MA (US); Bruce Carvalho, Watertown, MA (US); Andy Gover, Cambridge (GB); Roger Morris, Vero Beach, FL (US)

(73) Assignee: Vantix Holdings Limited, Cambridge (GB)

( * ) Notice: Subject to any disclaimer, the term of this patent is extended or adjusted under 35 U.S.C. 154(b) by 1172 days.

(21) Appl. No.: 12/045,611

(22) Filed: Mar. 10, 2008

(65) Prior Publication Data

US 2008/0217246 A1    Sep. 11, 2008

Related U.S. Application Data

(60) Provisional application No. 60/893,941, filed on Mar. 9, 2007, provisional application No. 60/955,791, filed on Aug. 14, 2007.

(51) Int. Cl.
*G01N 27/26* (2006.01)
*G01N 27/00* (2006.01)
*G01N 33/00* (2006.01)
*G01N 27/30* (2006.01)
*A61J 1/06* (2006.01)
*C25B 9/00* (2006.01)
*C12M 3/00* (2006.01)
*G01N 21/00* (2006.01)
*G01N 21/75* (2006.01)
*G01N 1/00* (2006.01)
*B01D 61/00* (2006.01)

(52) U.S. Cl.
USPC .... 422/554; 422/68.1; 422/82.01; 422/82.03; 422/63; 422/401; 435/287.2; 204/400; 204/403.01; 204/403.02; 204/403.03; 204/403.14; 210/645

(58) Field of Classification Search
USPC ............ 204/403.01, 403.14, 403.02, 403.03, 204/400; 422/68.1, 82.01, 82.03, 554, 401
See application file for complete search history.

(56) References Cited

U.S. PATENT DOCUMENTS

| | | |
|---|---|---|
| 4,933,092 A | 6/1990 | Aunet et al. |
| 5,096,669 A | 3/1992 | Lauks et al. |
| 5,100,626 A | 3/1992 | Levin |

(Continued)

OTHER PUBLICATIONS

International Search Report and Written Opinion for PCT/US08/56435 dated Jun. 30, 2008 (10 pages).

(Continued)

*Primary Examiner* — Brian J. Sines
*Assistant Examiner* — Jennifer Wecker
(74) *Attorney, Agent, or Firm* — Polsinelli PC

(57) ABSTRACT

An electrochemical detection system having a disposable cartridge capable of performing a plurality of assay protocols is disclosed. The cartridge includes a blister pack for the long-term storage and controlled release of multiple reagents. The blister pack is bonded to and operatively associated with a fluidic backbone for providing the fluid pathways, storage capacity, and fluid control functions for performing multiple assay protocols. The cartridge further includes a plurality of sensors having a multiple electrode arrangement in operative association with a respective flow cell defined by the fluidic backbone. After the user has transferred a sample into the cartridge and engaged the cartridge to the reader, the reader operatively interfaces with the cartridge such that different assay protocols may be simultaneously performed in isolation from one another inside the cartridge. The reader may be one of many readers that operatively communicate data to a remote server for processing.

16 Claims, 15 Drawing Sheets

(56) References Cited

U.S. PATENT DOCUMENTS

| | | | |
|---|---|---|---|
| 5,744,096 A * | 4/1998 | Jones et al. | 422/412 |
| 5,766,934 A | 6/1998 | Guiseppi-Elie | |
| 5,821,399 A | 10/1998 | Zelin | |
| 6,066,243 A | 5/2000 | Anderson et al. | |
| 6,176,962 B1 | 1/2001 | Soane et al. | |
| 6,391,622 B1 | 5/2002 | Knapp et al. | |
| 6,437,551 B1 | 8/2002 | Krulevitch et al. | |
| 6,438,498 B1 | 8/2002 | Opalsky et al. | |
| 6,444,461 B1 | 9/2002 | Knapp et al. | |
| 6,488,896 B2 | 12/2002 | Weigl et al. | |
| 6,548,263 B1 | 4/2003 | Kapur et al. | |
| 6,551,495 B1 | 4/2003 | Porter et al. | |
| 6,610,367 B2 | 8/2003 | Lewis et al. | |
| 6,623,860 B2 | 9/2003 | Hu et al. | |
| 6,770,190 B1 | 8/2004 | Milanovski et al. | |
| 6,774,643 B2 | 8/2004 | Magill | |
| 6,939,451 B2 | 9/2005 | Zhao et al. | |
| 6,966,880 B2 | 11/2005 | Boecker et al. | |
| 7,015,046 B2 * | 3/2006 | Wohlstadter et al. | 436/172 |
| 2002/0009390 A1 * | 1/2002 | Lappe et al. | 422/58 |
| 2002/0143298 A1 | 10/2002 | Marsden | |
| 2003/0034271 A1 * | 2/2003 | Burridge | 206/532 |
| 2003/0170881 A1 | 9/2003 | Davis et al. | |
| 2003/0199080 A1 | 10/2003 | Knoche | |
| 2004/0007461 A1 | 1/2004 | Edelbrock et al. | |
| 2004/0053290 A1 | 3/2004 | Terbrueggen et al. | |
| 2004/0129678 A1 | 7/2004 | Crowley et al. | |
| 2004/0175296 A1 | 9/2004 | Opalsky et al. | |
| 2004/0181528 A1 | 9/2004 | Tirinato et al. | |
| 2004/0189311 A1 * | 9/2004 | Glezer et al. | 324/444 |
| 2004/0260204 A1 | 12/2004 | Boecker et al. | |
| 2005/0009191 A1 | 1/2005 | Swenson et al. | |
| 2005/0106552 A1 | 5/2005 | Ikeda | |
| 2006/0144704 A1 | 7/2006 | Ghesquiere et al. | |
| 2006/0257993 A1 * | 11/2006 | McDevitt et al. | 435/287.2 |
| 2008/0217246 A1 | 9/2008 | Benn et al. | |
| 2009/0170187 A1 * | 7/2009 | Gundry | 435/287.6 |
| 2010/0304986 A1 * | 12/2010 | Chen et al. | 506/9 |

OTHER PUBLICATIONS

International Search Report and Written Opinion for PCT/US08/56414 dated Aug. 6, 2008 (10 pages).

E-mail from Elson [el_silva@uol.com/br], Subject Know-How and IP in Applied Hydrology (6 pages).

* cited by examiner

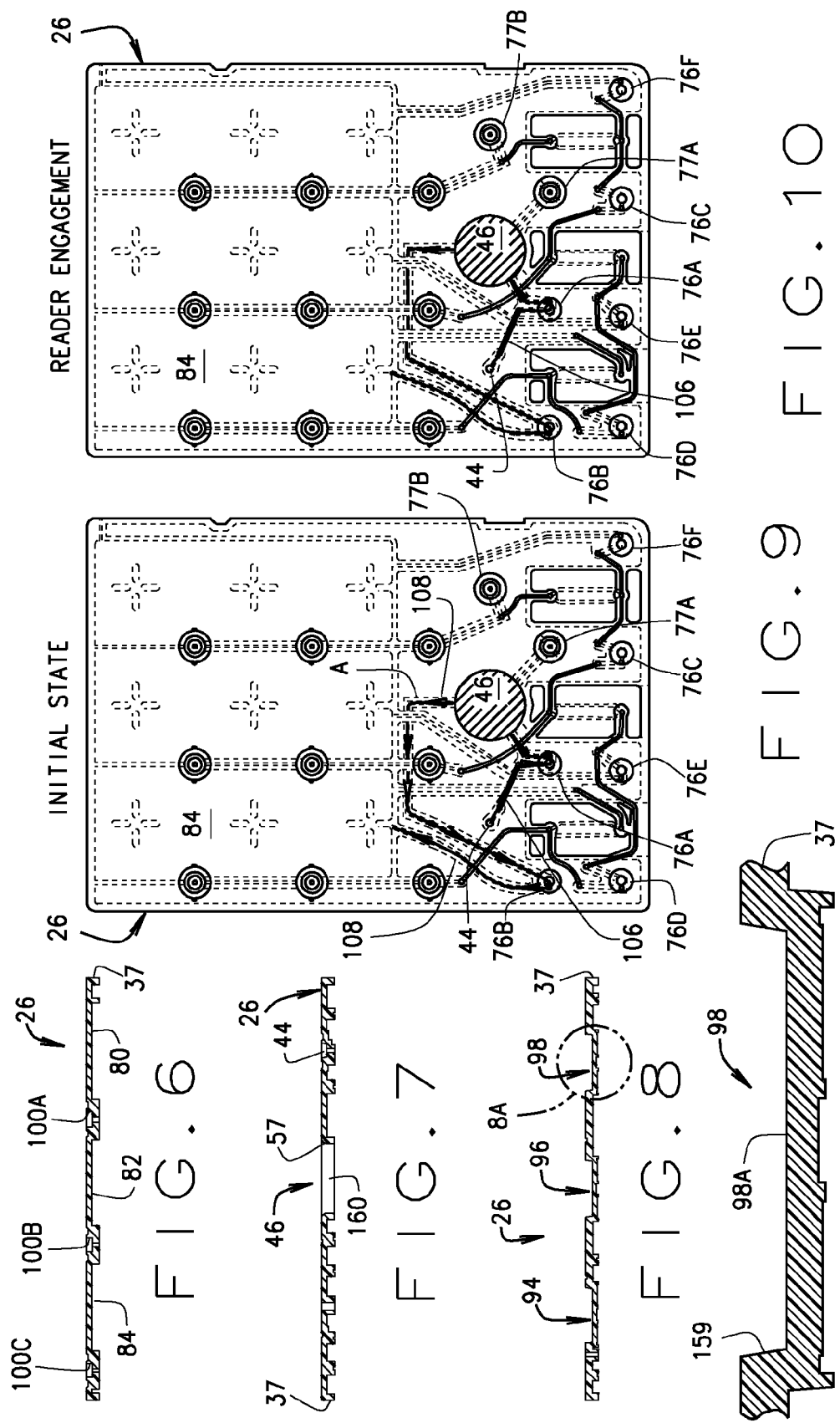

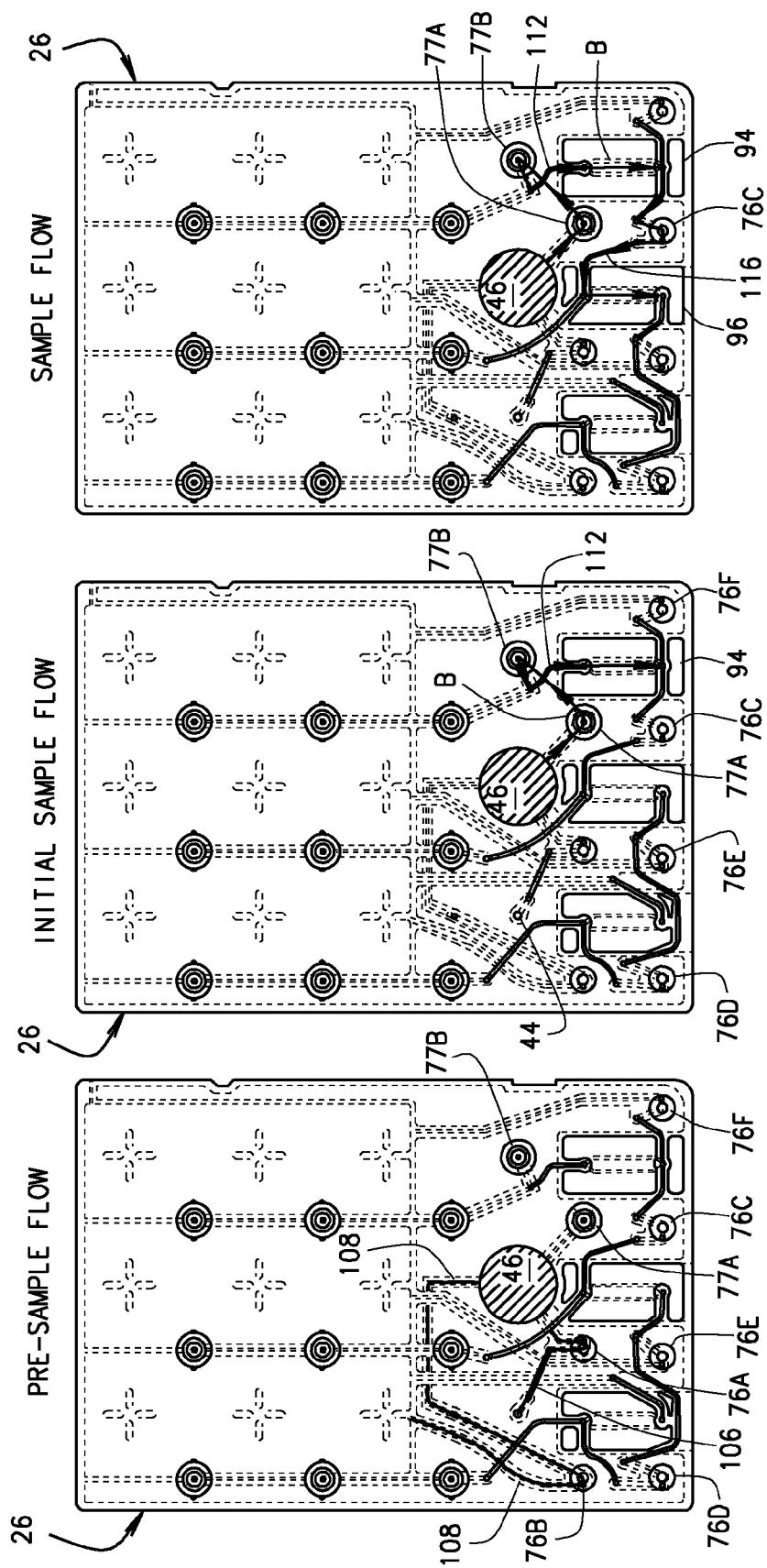

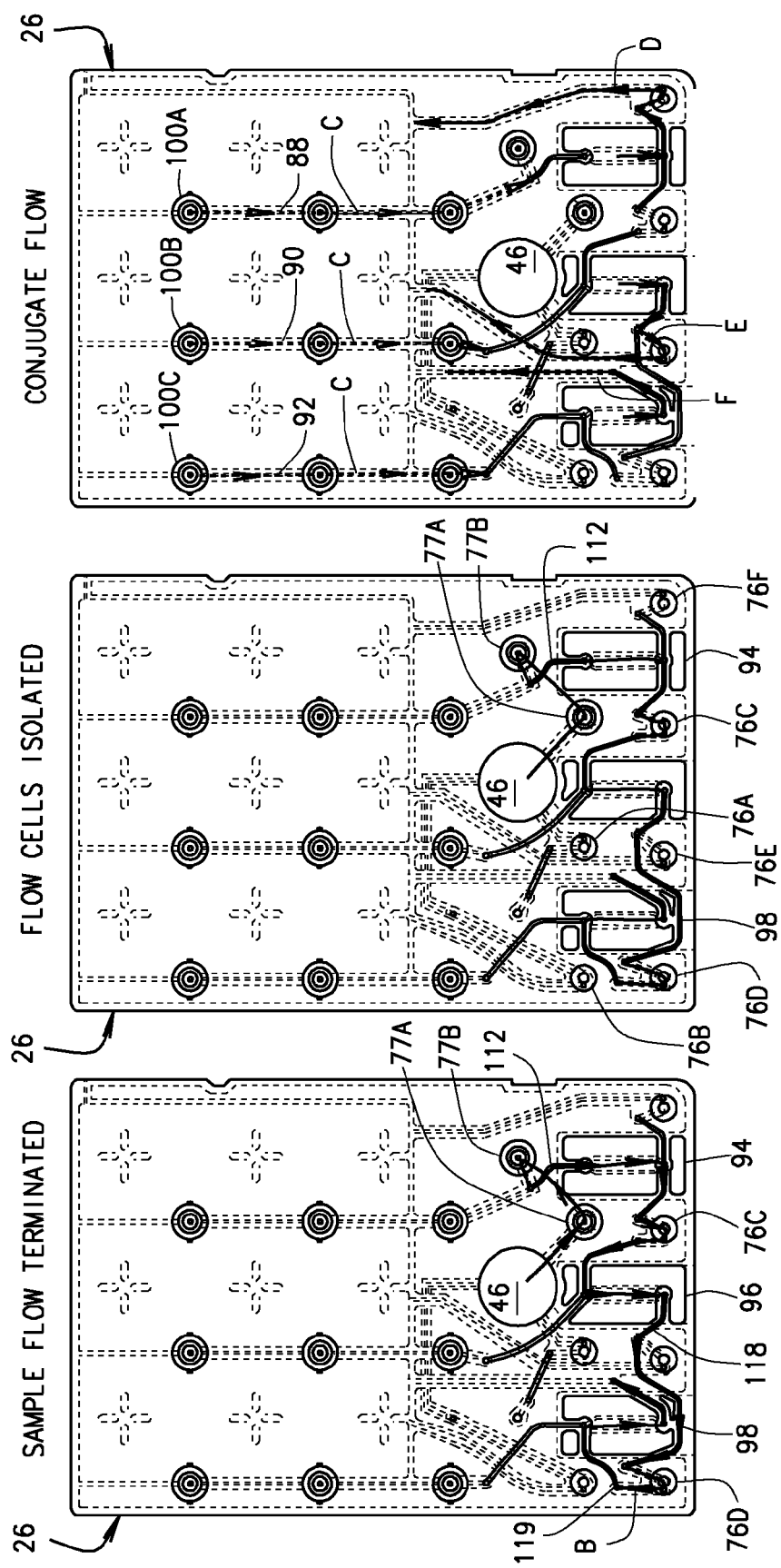

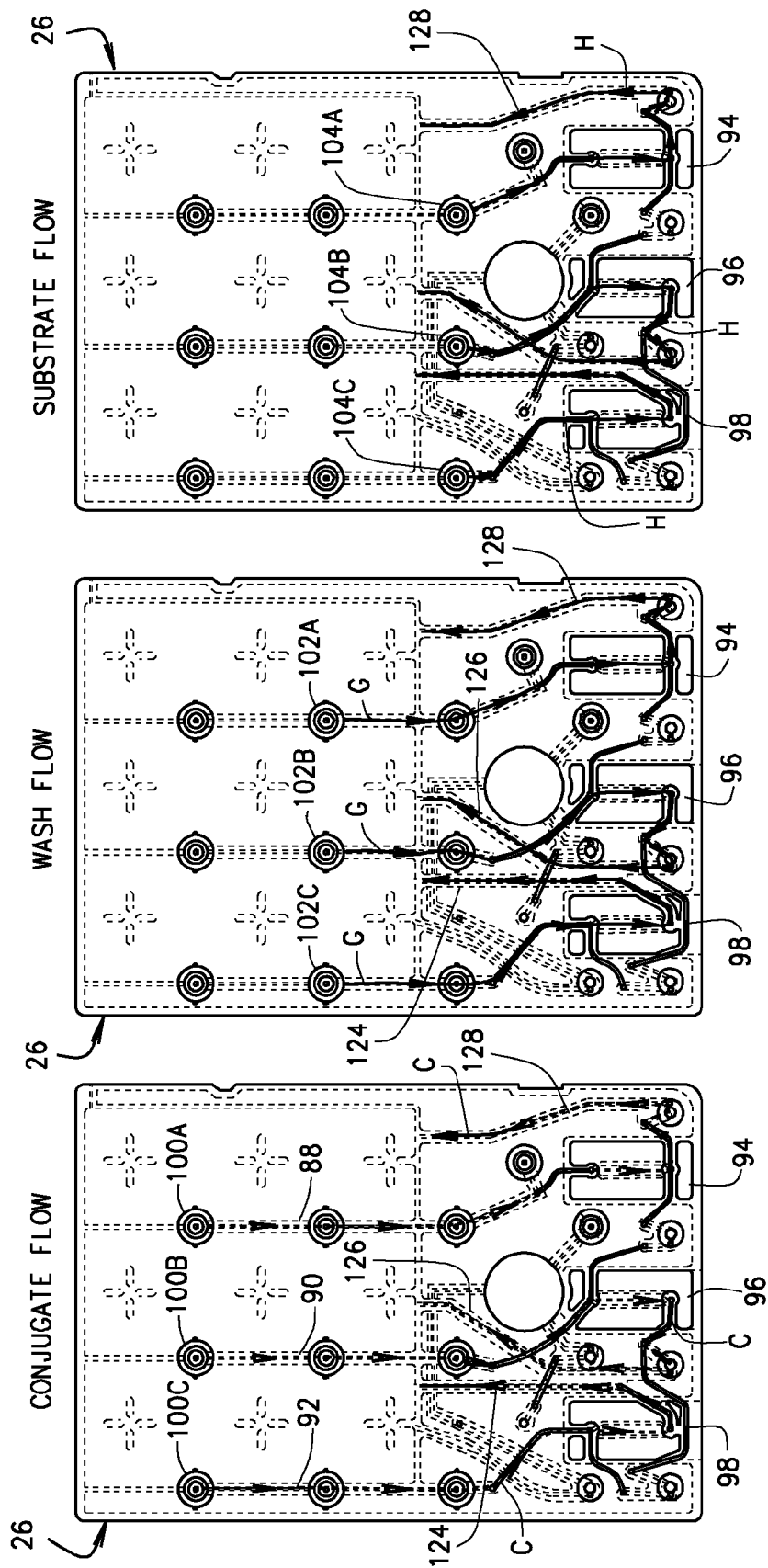

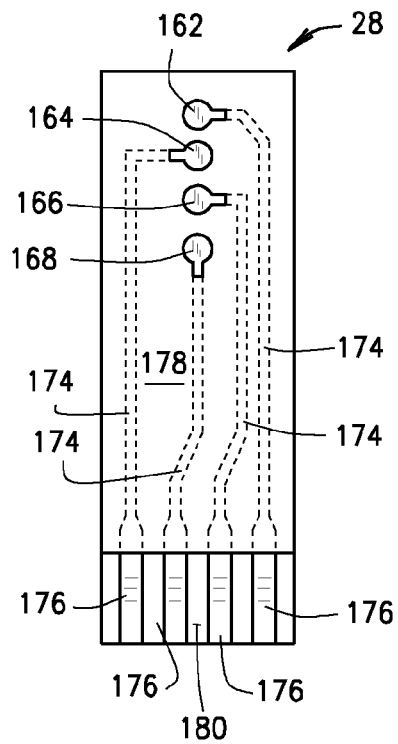
FIG.25
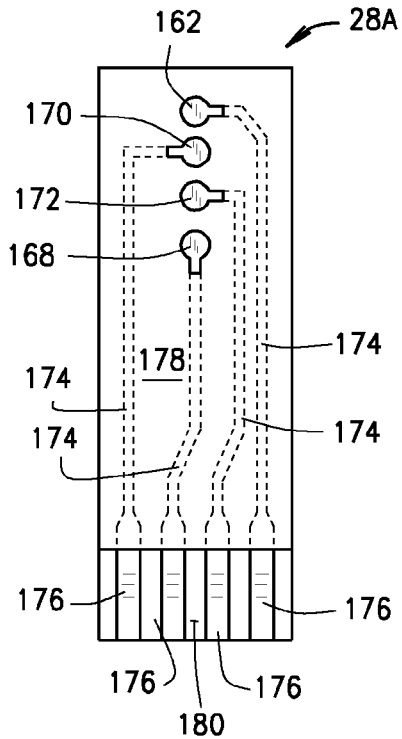
FIG.26
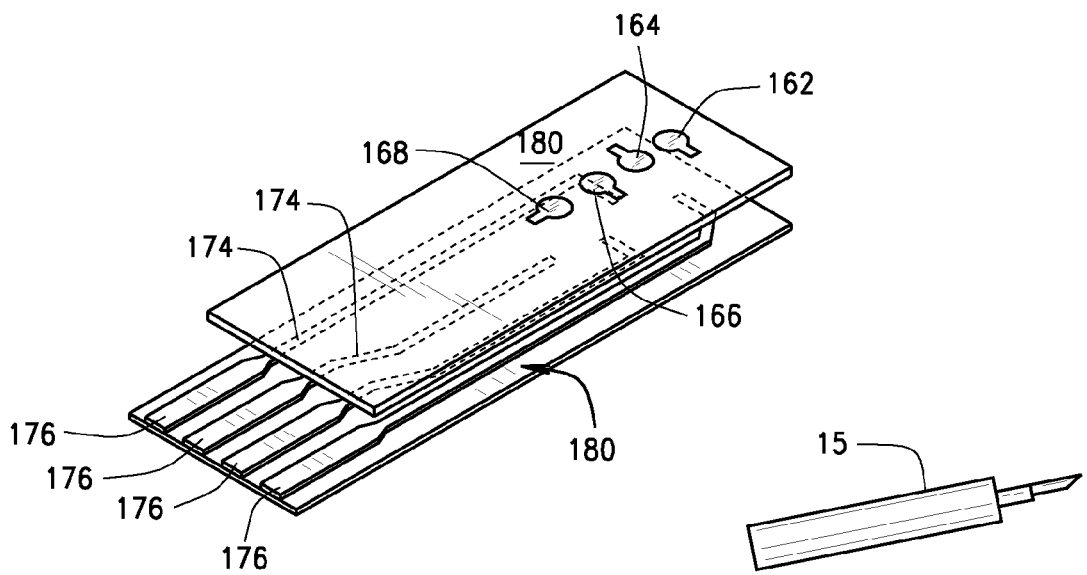
FIG.27
FIG.28

ELECTROCHEMICAL DETECTION SYSTEM

CROSS REFERENCE TO RELATED APPLICATIONS

The present application claims priority from U.S. provisional patent application Ser. No. 60/893,941 entitled "Cartridge for a Point of Care Diagnostic System and Method" filed on Mar. 9, 2007 and U.S. provisional patent application Ser. No. 60/955,791 entitled "Electrochemical Detection System having a Cartridge and Reader Device Arrangement" filed on Aug. 14, 2007, both of which are herein incorporated by reference in their entirety.

FIELD

This document relates to an electrochemical detection system for conducting electrochemical analysis, and more particularly to an electrochemical detection system having a cartridge adapted to engage a reader device for performing multiple assay protocols.

BACKGROUND

Electrochemistry is a branch of chemistry that studies chemical reactions that take place in a solution at the interface of an electron conductor (e.g., electrode composed of a metal or semiconductor material) and an ionic conductor (e.g., electrolyte), and which involve electron transfer between the electrode and the electrolyte or species in solution.

If an external applied voltage drives the chemical reaction, or a voltage is created by the chemical reaction, it is called an electrochemical reaction. Chemical reactions where electrons are transferred between molecules are called oxidation/reduction (redox) reactions. In general, electrochemistry relates to situations where oxidation and reduction reactions are separated in space and time, connected by an external electric circuited used to understand the reaction that is occurring.

Electrochemical analysis using a disposable cartridge containing a reagent for inducing an electrochemical reaction that may be detected by a sensor is known in the art. In particular, the cartridge may be operatively engaged to a reader device that initiates an assay protocol by mechanically actuating the cartridge and receives data signals for obtaining the test results of the assay performed within the cartridge. The cartridge may define a plurality of fluidic channels that transport the sample and reagent to a flow cell for performing the assay and waste chamber for collection of sample and reagent waste. The cartridge may further include a flow control arrangement, such as valves, to control the flow of the sample and reagent through the cartridge during performance of the assay protocol. In addition, the flow cell may include a sensor arrangement for detecting signals generated during the performance of the assay protocol on the sample and transmit those signals to the reader device.

Although such disposable cartridges have provided adequate platforms for performing a particular assay protocol, there is a need in the art for a more versatile and robust cartridge that may perform multiple assay protocols. In addition, there is a need in the art for an electrochemical detection system that permits a plurality of readers to operatively communicate with a remote server for the processing of data generated by performance of a plurality of assay protocols.

SUMMARY

In one aspect, the electrochemical detection system includes a cartridge for performing a plurality of assay protocols. The cartridge includes a blister pack having a plurality of deformable blister domes that store a respective liquid and permit the controlled release of the liquid for performing multiple assay protocols when the blister domes are deformed due to mechanical actuation. The blister domes are in fluid flow communication with a frangible puncture valve site through a finger channel that establishes a fluidic pathway between the blister dome and the puncture valve site. When the cartridge is operatively engaged to a reader, the puncture valve site may be mechanically actuated by the application of a mechanical force to the puncture valve site that breaks apart and establishes fluid flow communication between the blister domes and various fluidic channels in the cartridge. To provide for the controlled release of the liquids within the cartridge, the reader mechanically then actuates one or more of the blister domes to permit the flow of liquid through from the blister domes and into the fluidic channels.

The blister pack is bonded to a fluidic backbone by a flexible adhesive film with the fluidic backbone providing the necessary structural elements for establishing fluidic pathways, fluid flow control and performance of assay protocols. A bottom lid is engaged to the fluidic backbone for providing certain structure elements defining the various fluidic pathways of the cartridge. In addition, the fluidic backbone includes a plurality of flow cells adapted to receive a sample after the sample has been stored in a sample reservoir within the cartridge using a sample transfer device. The flow cells are also adapted to receive one or more reagents across each flow cell for simultaneously performing multiple assay protocols. A sensor is operatively associated with each flow cell for performing a particular assay protocol when engaged to a reader that mechanically actuates the cartridge and obtains sensor readings and other data that may be transmitted to a remote server for obtaining a test result.

In another aspect, the electrochemical detection system includes a reader adapted to operatively engage the cartridge for initiating the simultaneous performance of a plurality of assay protocols. The reader includes a body having one or more docking stations adapted to operatively engage a respective cartridge for performing the assay protocols. In addition, the reader includes a plurality of mechanical actuators, such as pistons or rollers, that engage different portions of the cartridge, such as the blister domes, puncture valve sites, sample reservoir and valves sites for initiating and controlling fluid flow through the cartridge. The reader is also capable of receiving signals generated by the sensors in the cartridge and transmitting those signals to a remote server for processing the reader may process the signals for obtaining a test result. A control panel and screen are also provided as a user interface for the reader. In the alternative, the reader may also process the signals and data generated by the operation of the cartridge.

In a further aspect, the electrochemical detection system includes a method for performing a plurality of assay protocols on a single cartridge. The method includes providing a cartridge having a plurality of flow cells that receive the same sample, but then the flow cells are later isolated from each other in order to receive reagent liquids for performing the plurality of assay protocols. In this manner, different assay protocols may be simultaneously performed on a single cartridge as well as a single sample can be analyzed for multiple analytes.

In yet another aspect, the electrochemical detection system includes a sensor for use in electrochemical analysis of a plurality of assay protocols. The sensor may include a four-electrode arrangement having a sample working electrode, two calibration working electrodes and a reference electrode constructed using four separate layers that are screen printed to produce a sensor design on a flexible insulating substrate. In the alternative, the sensor may have a three sample electrodes and reference electrode arrangement.

To construct the sensor, electrically conductive silver tracks are screen printed followed by a silver/silver chloride reference electrode. Once the conductive silver tracks and reference electrode are screen printed, a carbon working electrode may then be screen printed for each electrode followed by the application of a dielectric layer that covers the areas outside of the working and reference electrodes. The dielectric layer also covers the conductive silver tracks to prevent liquid from coming into contact with the conductive tracks during performance of the assay protocol; however, the dielectric layer does not cover the conductors that operatively engage the electrodes to a reader for transmitting signals from the sensor.

In one aspect, the electrochemical detection system includes a software component that is capable of processing the signals and data generated by the cartridge during the performance of assay protocols. The software component may employ methodologies and algorithms to process the data generated by the performance of an assay protocol in order to provide a test result to the user. In one embodiment, the software component may incorporated into a reader that is operatively engaged with the cartridge for processing data and managing the operation of the cartridge, or the software component may be incorporated into a remote server that is in operative communication with the reader.

In another aspect, the electrochemical detection system includes a plasma separation component in the cartridge or sample transfer device that utilizes a glass fiber filter to extract plasma from a whole blood sample either before or after the entry of the sample into the cartridge. The extraction of plasma from the whole blood sample may be accomplished by allowing the whole blood sample to wick through the glass fiber filter for a predetermined amount of time. In one embodiment a working fluid may be used to flush the plasma from the glass fiber filter after the whole blood sample is allowed to wick through the glass fiber filter for the predetermined amount of time. The plasma may then be stored in the sample reservoir for controlled release to a plurality of flow cells contained within the cartridge after engagement to a reader.

In a further aspect, the electrochemical detection system includes a cartridge having top and bottom sides. The cartridge is adapted to engage a reader that mechanically actuates the cartridge from only the top or bottom side of the cartridge. In one embodiment, the side opposite that being mechanically actuated by the reader may have a heating source applied to that side for thermal control of the cartridge.

In one aspect, the electrochemical detection system includes a method of manufacturing a blister pack having a deformable top portion adapted to deform, but not break, upon mechanical actuation and a frangible bottom portion that breaks apart upon application of the same mechanical force. The deformable upper portion of the blister pack may include a plurality of blister domes for storing liquids made using a cold forming process. Liquids are then added to the cold formed blister domes and a lid provided to seal the frangible foil to the cold formed material. Typically, heat and pressure techniques are used to seal the upper and lower portions of the blister pack.

In another aspect, heat and pressure sealing processes may be applied to the blister pack outside the areas that form the blister dome, finger channels, puncture valve sites and valve sites. In these areas, the use of patterned heat and pressure processes to seal the deformable upper portion to the frangible lower portion defines a fluidic pathway between the deformable upper portion and frangible lower portion. The application of a mechanical force to the blister back will cause the deformable upper portion to deform while breaking apart the frangible lower portion for establishing fluid flow communication.

In yet another aspect, the electrochemical detection system includes a disposable cartridge having a blister pack operatively engaged with a fluidic backbone for controlling the flow of fluid within the cartridge. The blister pack defines a plurality of valve sites that correspond to a respective plurality of valves defined by the fluidic backbone. Each of the plurality of valve sites includes a deformable upper portion and a frangible lower portion of the blister pack adapted to deform when mechanically actuated. The valve defines an inlet in selective fluid flow communication with an outlet through a well that includes a raised rim that surrounds the inlet. In operation, the cartridge is adapted to operatively engage a reader that mechanically actuates the flexible valve site by forcing the value site against the raised rim to prevent fluid flow communication through the valve, while disengagement of the valve site from the raised rim permits fluid flow communication between the inlet and the outlet of the valve. In this manner, the flow of fluid through the cartridge is controlled and managed by the reader by selectively engaging specific portions of the blister pack against the fluidic backbone.

In a further aspect, the electrochemical detection system may include one or more readers adapted to engage a respective cartridge for performing simultaneous assay protocols. The readers may be in operative communication with a remote server for establishing a point of care system that transmits data from the readers to the remote server for processing and providing a test result to a particular reader.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 3A is a structural schematic of the deformable upper portion of the blister pack;

FIG. 3B is a structural schematic of the frangible lower portion of the blister pack;

FIG. 6 is a cross-sectional view taken along line 6-6 of FIG. 5 showing the waste chambers and puncture site bases of the fluidic backbone;

FIG. 7 is a cross-sectional view taken along line 7-7 of FIG. 5 showing the sample reservoir of the fluidic backbone;

FIG. 8 is a cross-sectional view taken along line 8-8 of FIG. 5 showing the flow cells and fluidic channels of the fluidic backbone;

FIG. 8A is an enlarged cross-sectional view of the fluidic backbone showing the structural aspects of the flow cell;

FIG. 9 is a schematic view of the fluidic backbone illustrating the flow of sample during the transfer of sample into the sample reservoir of the cartridge;

FIG. 10 is a schematic view of the fluidic backbone illustrating the open/closed condition of the valves after the sample has been stored in the sample reservoir and prior to engagement of the cartridge with the reader;

FIG. 11 is a schematic view of the fluidic backbone during initial engagement of the cartridge with the reader;

FIGS. 12-14 are schematic views of the fluidic backbone that illustrate the sequence of sample flow from the sample reservoir through the first, second, and third flow cells of the cartridge;

FIG. 15 is a schematic view of the fluidic backbone illustrating isolation of the first, second, and third flow cells of the cartridge;

FIGS. 16-17 are schematic views of the fluidic backbone illustrating the sequence of conjugate fluid flow through the first, second, and third flow cells;

FIG. 18 is a schematic view of the fluidic backbone illustrating the flow of washing fluid through the first, second, and third flow cells;

FIG. 19 is a schematic view of the fluidic backbone illustrating the flow of substrate fluid through the first, second, and third flow cells;

FIG. 25 is a top view of the sensor arrangement used in the cartridge for electrochemical detection;

FIG. 26 is a top view of another embodiment of the sensor arrangement used in the cartridge for electrochemical detection;

FIG. 27 is an exploded view of the sensor arrangement shown in FIG. 25;

FIG. 28 is a side view of a sample transfer device used to transfer the sample to the cartridge;

Corresponding reference characters indicate corresponding elements among the view of the drawings. The headings used in the figures should not be interpreted to limit the scope of the claims.

DETAILED DESCRIPTION

Figure 1:
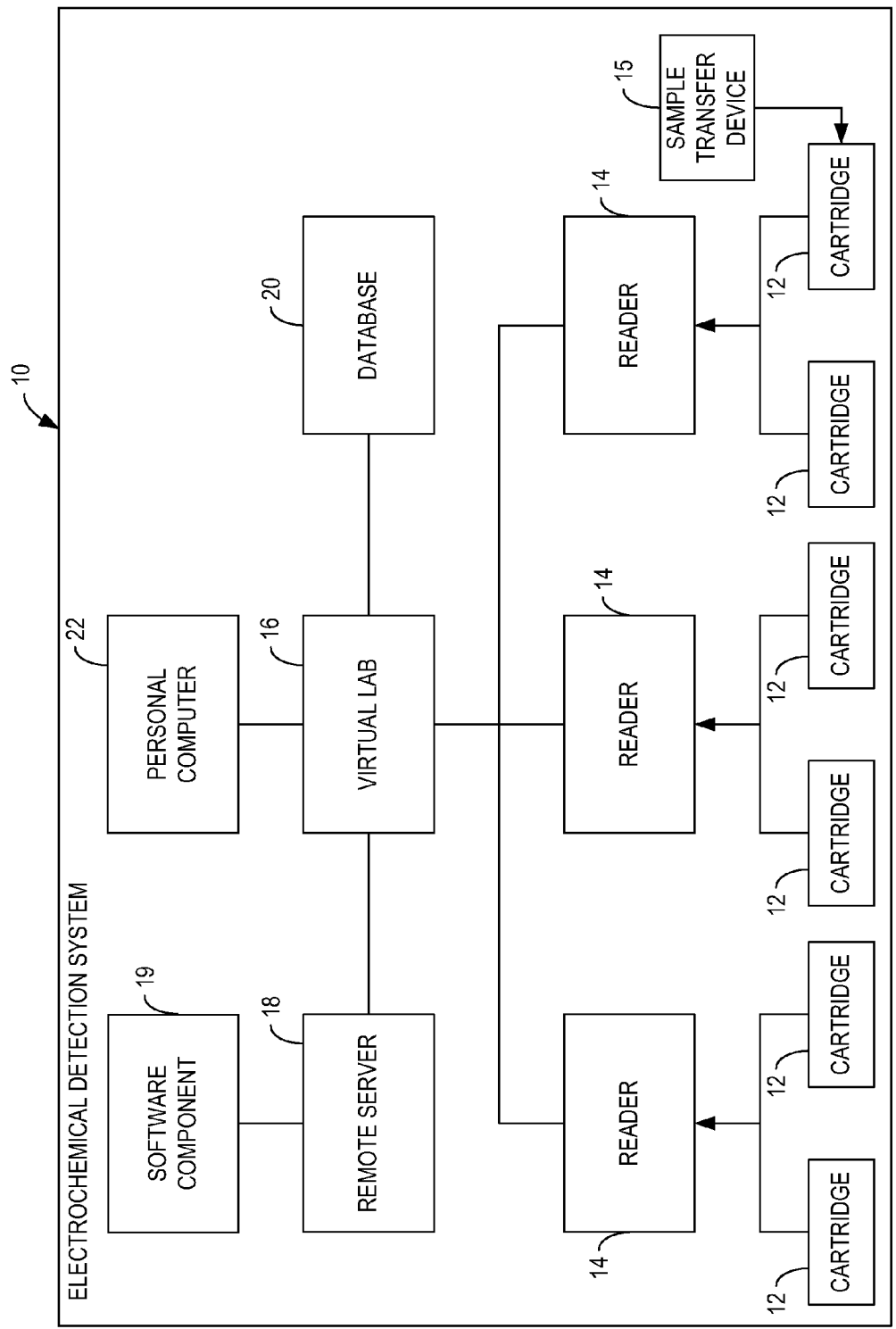
FIG. 1 is simplified block diagram illustrating the different components of the electrochemical detection system.

Referring to the drawings, an embodiment of the electrochemical detection system is illustrated and generally indicated as 10 in FIG. 1. The electrochemical detection system 10 provides a means for conducting a plurality of assay protocols on a single disposable cartridge 12 when operatively engaged to a reader 14. In addition, the electrochemical detection system 10 may include a plurality of readers 14 that are in operative communication with a virtual lab 16 for communicating data, such as test results or calibration information, between the readers 14 and a remote server 18 associated with the virtual lab 16.

The remote server 18 may also be in operative communication with a database 20 for the storage of data transmitted by the readers 14 and a software component 19 for processing of the data transmitted by the readers 14. In the alternative, the software component 19 may be incorporated into the reader 14. Moreover, a personal computer 22 may be used to interface with the virtual lab 16 for accessing data stored in the database 20. Finally, a sample transfer device 15 may be utilized to transfer a sample, such as whole blood, to the cartridge 12 for analysis as shall be discussed in greater detail below.

Figure 2:
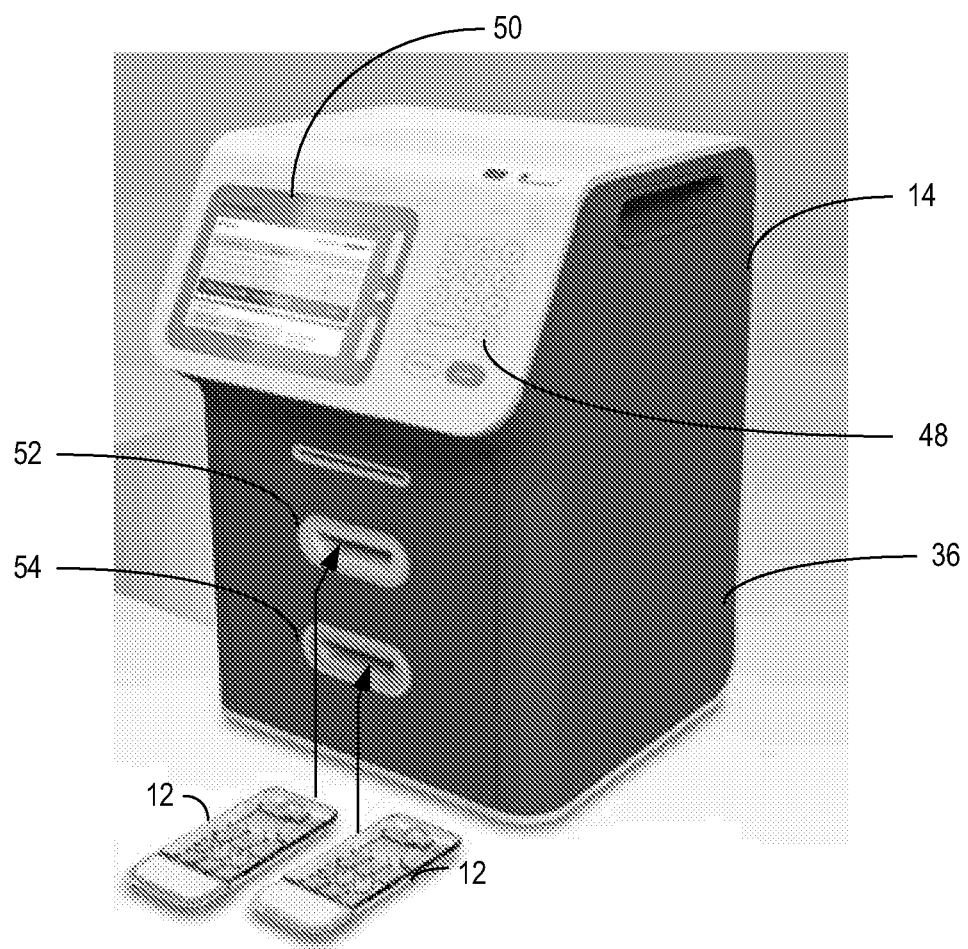
FIG. 2 is a simplified illustration showing the cartridge and reader arrangement.

As shown in FIG. 2, each reader 14 may include a reader body 36 having a control panel 48 that permits the user to perform a plurality of assay protocols when a respective cartridge 12 is operatively engaged to the reader 14. In one embodiment, the reader 14 may include a first docking station 52 and a second docking station 54 for operative engagement of a respective cartridge 12 with the reader 14, although other embodiments of the reader 14 may include one or more docking stations for engaging any number of respective cartridges 12. The reader 14 further includes a screen 50 that acts as a user interface and a communication component (not shown) that permits the reader 14 to operatively communicate with the virtual lab 16 through the remote server 18.

As illustrated in FIGS. 21-24, each docking station 52 and 54 includes respective actuating pistons 132, 136, 138 and 142 for operative engagement with particular portions of the cartridge 12 to provide fluid flow control and controlled release of liquids contained in the cartridge 12 as shall be discussed in greater detail below. In one embodiment, the actuating pistons 132, 136, 138 and 142 may be driven and controlled by the reader 14 using a cam-driven mechanism (not shown) that includes one or more stepper motors. In addition, the actuating pistons 132, 136, 138 and 142 may be made from steel, caste aluminum or other hard material, however the actuating pistons 132, 136, 138 and 142 may be made from a flexible elastomeric material. In the alternative, the pistons 132, 136, 138 and 142 may be rollers that are used to mechanically actuate the cartridge 12 as described above.

Figure 3:
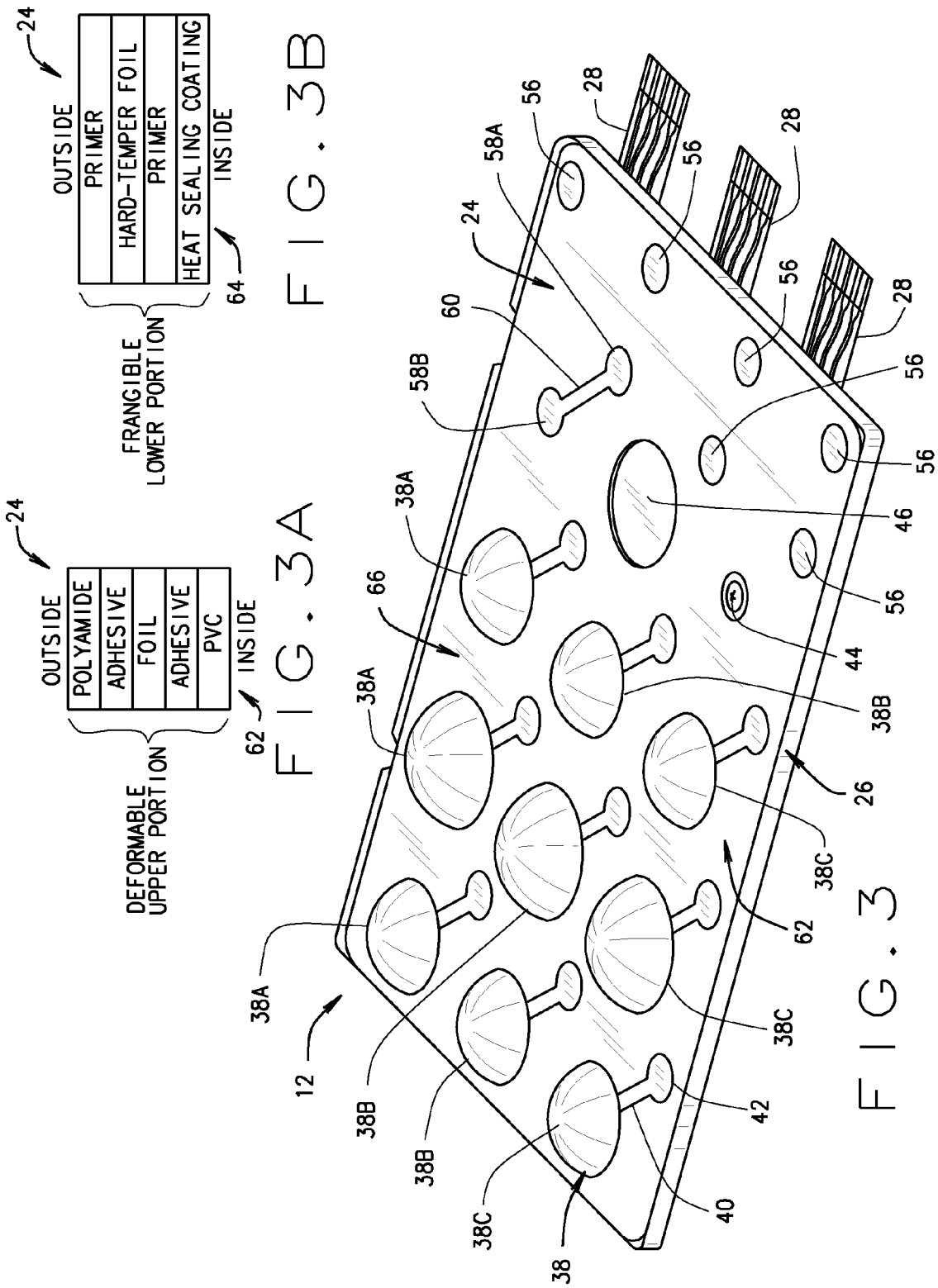
FIG. 3 is a perspective view of the cartridge showing the blister pack.
Figure 4:
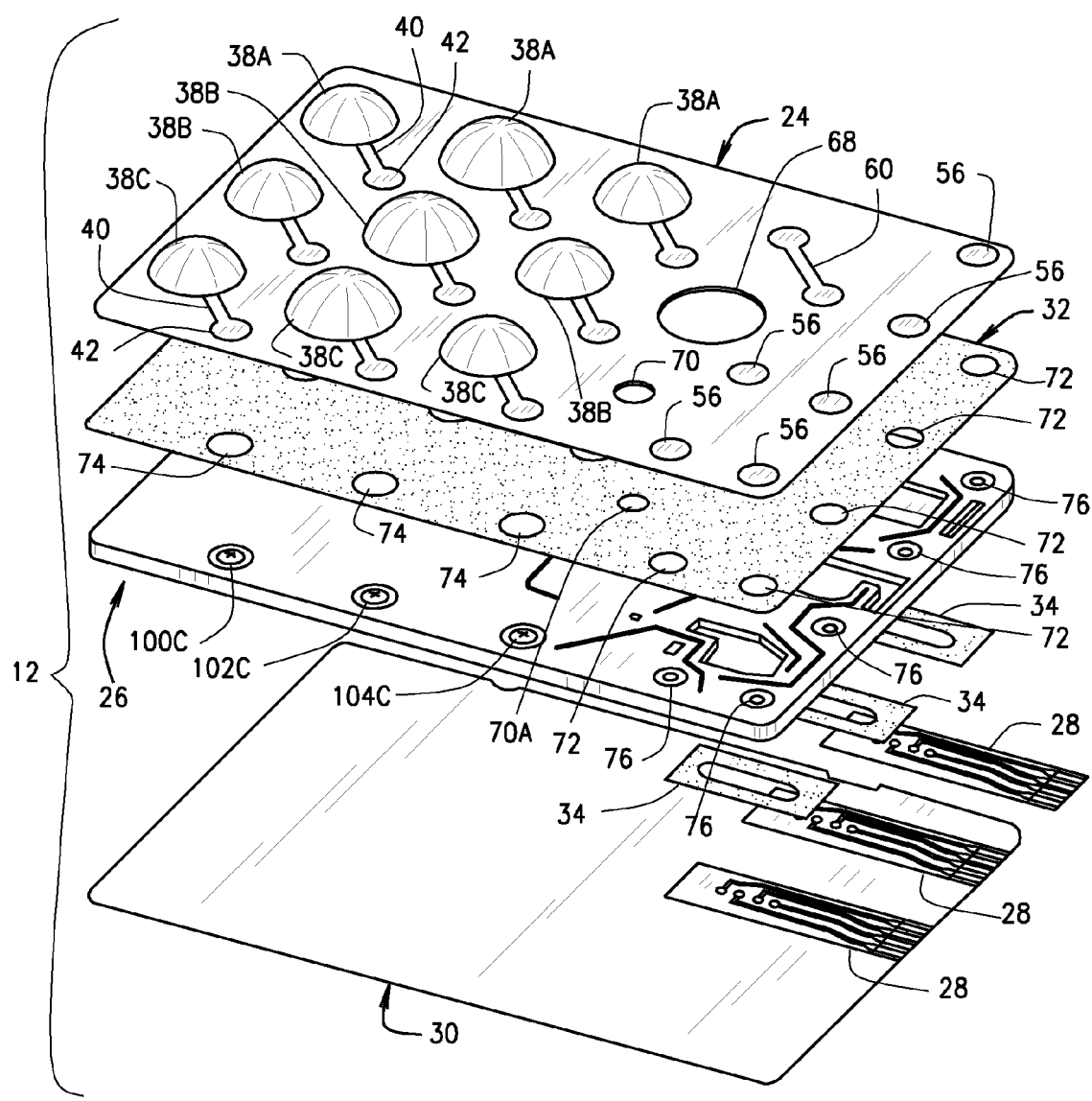
FIG. 4 is an exploded view of the cartridge showing the blister pack, fluidic backbone, sensors, and bottom lid components.

Referring to FIGS. 3 and 4, the structural details of the cartridge 12 will be discussed. The cartridge 12 includes a blister pack 24 adapted for the storage and controlled release of a plurality of liquids, such as reagents, and/or gases. The blister pack 24 is bonded to a fluidic backbone 26 through a double-sided adhesive film 32. The adhesive film 32 defines valve cutouts 72 and puncture valve site cutouts 74 that allow operational and structural interaction between the blister pack 24 and the fluidic backbone 26. In addition, the adhesive film 32 defines an input port adhesive cutout 70A that aligns with an input port blister pack cutout 70 of the fluidic backbone 26 when the cartridge 12 is assembled for permitting access to input port 42 of cartridge 12. As shown, the fluidic backbone 26 provides the various fluidic channels, valves, storage chambers, and flow cells used to perform a plurality of assay protocols by the cartridge 12.

The cartridge 12 further includes a plurality of sensors 28 bonded to the fluidic backbone 26 by sensor adhesive cutouts 34. In addition, a bottom lid 30 may be engaged to the fluidic backbone 26 for collectively defining the various channels and chambers of the cartridge 12. In one embodiment, the bottom lid 30 may be an extruded film that is bonded to the fluidic backbone 26. However, a top lid (not shown) may also be provided for completely encasing the cartridge 12 and to also prevent inadvertent contact with the blister pack 24.

Figure 24:
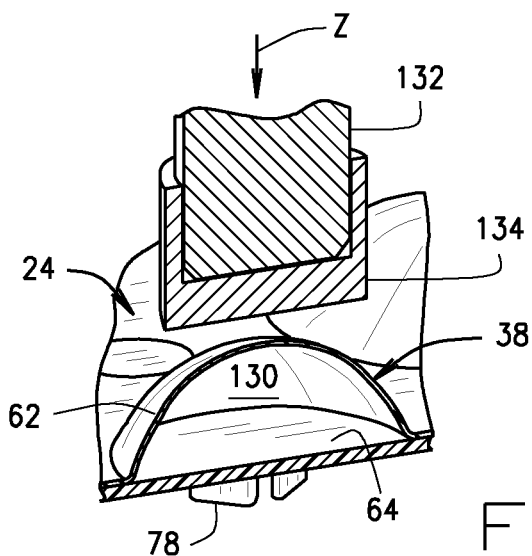
FIG. 24 is a cross-sectional view showing a piston of the reader engaging the blister dome of the blister pack for the controlled release of liquid into the fluidic backbone.

Referring to FIGS. 3A and 3B, the blister pack 24 includes a deformable upper portion 62 and a frangible lower portion 64 that are selectively bonded together using a sealing process that permits specific areas of the upper portion 62 to remain free from the frangible lower portion 64, thereby providing fluidic pathways have a particular configuration. In particular, the sealing process may produce a plurality of deformable blister domes 38 that provide long term platforms for the storage of various respective liquids, such as conjugate, wash and substrate liquids used to perform a plurality of assay protocols. As shown in FIG. 24, each blister dome 38 defines a storage chamber 130 between the deformable upper portion 62 and frangible lower portion 64 for storing a liquid with the blister dome 38 resting on a support base 78 defined along the fluidic backbone 26. The support base 78 provides the necessary structural support required for the reader 14 to mechanically actuate the opposite side of the blister dome 38 to provide for the controlled release of the stored liquids. In one embodiment, the blister domes 38 that store the conjugate and wash liquids may have maximum volumes of 270 µL, while the blister domes 38 that store the wash may have a maximum volume of 516 µL. In another embodiment, the blister domes 38 may have a storage capacity ranging from 10 µL to 1 mL.

The storage chamber 130 of the blister dome 38 is in fluid flow communication with a finger channel 40 that extends from the blister dome 38 and terminates at a puncture valve site 42. The finger channel 40 and puncture valve site 42 are both related to a respective blister dome 38 and define a fluidic pathways between the deformable upper portion 62 and frangible lower portion 64 of the blister pack 24 that are not sealed together. The puncture valve site 42 acts as a release point for the controlled release of the reagent liquid from each respective blister dome 38 when the blister dome 38 and its related puncture valve site 42 are sequentially actuated by the reader 14 as shall be discussed in greater detail below.

Figure 29:
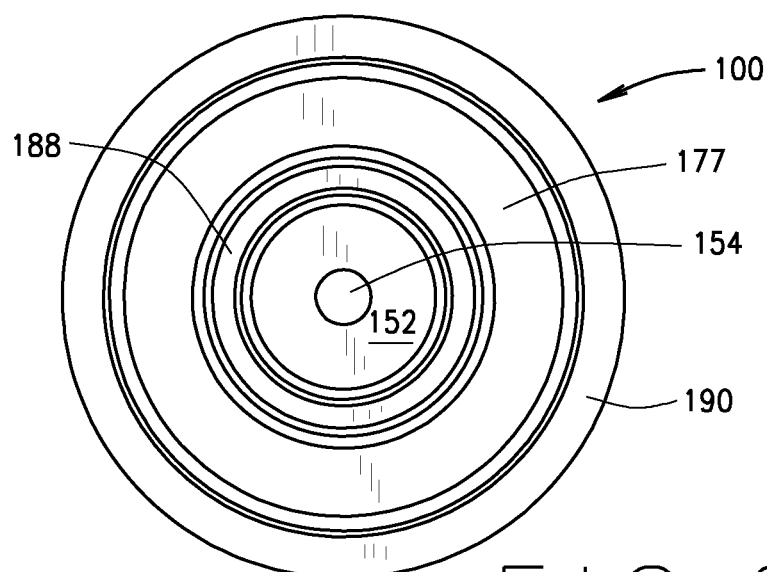
FIG. 29 is a plan view of the puncture defined by the fluidic backbone.

For purposes of illustration only puncture valve site base 100 will be discussed in reference to FIGS. 23, 23A and 29 to show the various structural elements and operation of the puncture valve site. As shown, the fluidic backbone 26 includes a puncture valve site base 100 that defines a recessed well 152 in fluid flow communication with an outlet 154 that may lead to one of the main channels 88, 90 and 92. A raised inner rim 188 and raised outer rim 190 surrounds the recessed well 152 with a channel 177 defined between the inner and outer rims 188, 190. In the normally closed position, the puncture valve site 42 of the blister pack 24 is engaged against the inner and outer raised rims 188 and 190 of the puncture site base 100 such that fluid from the blister dome 38 is sealed between the upper and lower portions 62 and 64 and fluid flow communication with the outlet 154 is prevented.

When the puncture piston 142 with an elastomeric boot 146 is moved in the Z direction by the reader 14 and mechanically actuates the puncture valve site 42 the deformable upper portion becomes deformed or elongated while the frangible lower portion 64 breaks apart to establish fluid flow communication between the finger channel 40 and recessed well 152. In particular, engagement of the elastomeric boot 146 as the puncture piston 142 is forced against the puncture valve site 42 pinches the valve site 42 between the boot 140 and the raised inner rim 188 such that the raised inner rim 188 acts as a structural support. This causes the upper portion 62 of the blister pack 24 in the area of the puncture valve site 42 to deform while allowing the frangible lower portion 64 to break apart and thereby establish fluid flow communication between the blister dome 38 and the outlet 154.

Once the frangible lower portion 64 breaks apart, the elastomeric boot 146 maintains engagement and seals the area of the puncture valve site 42 against the raised inner rim 188 and ensures that fluid does not leak from the puncture valve site 42 by sufficiently covering the recess well 152 with the blister pack 24. This fluid tight seal between the puncture valve site 42 and the puncture site base 100 is maintained even when the blister dome 38 is mechanically actuated by the reader 14 to release fluid through the finger channel 40 and through the outlet 154 of the puncture valve site base 100. To provide for the controlled release of fluid from the blister dome 38 through the outlet 154, the puncture piston 142 is retracted from the puncture site base 100 and reader 14 mechanically actuates the blister dome 38 by applying a force by the dome piston 132 in a manner that deforms the upper portion 62 and breaks apart the lower portion 64 of the blister pack 24 as shown in FIG. 24. In one embodiment, the dome piston 132 may include an elastomeric boot 134 that is sufficiently flexible when engaged to the sample reservoir 46. As such, the controlled release of liquid may be a two-step process requiring the reader 14 to mechanically actuate the puncture valve site 42 followed by the mechanical actuation of the blister dome 38 to positively displace the liquid from the blister dome 38 and through the opened puncture valve site 42.

As noted above, the deformable upper portion 62 of the blister pack 24 becomes deformed, but does not break, when the reader 14 applies a mechanical force to the blister pack 24. In contrast, the frangible lower portion 64 will break apart when the reader 14 applies that same force to the blister pack 24. As such, the deformable upper portion 64 of the blister pack 24 is designed to withstand more elongation before breaking when a mechanical force is applied than the frangible lower portion 64 that will readily break apart. For example, it has been found that elongations of the upper and lower portions 62, 64 that range between 11% and 21% result in the frangible lower portion 64 breaking, while the deformable upper portion 62 deforms but does not break. This difference in elongation properties exhibited by the upper and lower portions 62 and 64 effectively prevents fluid from leaking from the deformed upper portion 62 when mechanically actuated, but will allow fluid flow communication between the blister pack 24 and fluidic backbone 26 as the lower portion 64 breaks apart under the same mechanical actuation applied to the same area of the pack 24 by the reader 14.

The blister pack 24 may be fabricated by forming the blister domes 38, finger channels 40, puncture valve sites 42, and valve sites 56 in the cold formable material, such as COLD FORM™ 3000 made by Alcoa. As shown in FIG. 3A, the cold formable material may be a composite film made from a polyamide layer bonded to an aluminum foil that is bonded to a PVC film. Each of these layers has a defined function. In particular, the aluminum foil provides excellent barrier properties and allows for the long term storage of liquids, such as reagents, while the polyamide layer provides support to the aluminum foil during the cold forming process; thereby, allowing the aluminum foil to elongate further than if the aluminum foil was unsupported by the polyamide layer. Finally, the PVC film provides a heat sealable medium for standard blister pack 24 sealing materials.

In the cold forming process, the cold formable material is first drawn over a bottom platen (not shown) and then clamped or sandwiched between a top platen. The bottom platen has one or more holes that are aligned with pistons or other mechanical devices (not shown) in the top platen. The cold formable material is oriented so that the polyamide layer or other mechanical support layer faces the bottom platen and the PVC layer or other sealable layer faces the top platen. The pistons are then driven into the clamped cold formable material, thereby drawing the composite film and forming the blister domes 38, finger channels 40, puncture valve sites 42, dog bone channel 60, normally-closed valves valve sites 58A and 58B, and valve sites 56. After forming these features, liquids may then be dispensed into each of the blister domes 38 for storage. Finally, the liquid-filled blister domes 38 are sealed along the frangible lower portion 64. The result is that the blister pack 24 consists of a plurality of cold formed blister domes 38 that separately encapsulate fluids and sealed with the frangible lower portion 64 of the blister pack 24. This arrangement permits the separate storage of a plurality of liquids for controlled release to a plurality of isolated flow cells 94, 96 and 98 of cartridge 12.

As noted above, the deformable upper portion 62 may be made from COLD FORM™ 3000 by Alcoa, however the frangible lower portion 64 may be made from DRUG PAK 841 also by Alcoa. As shown in FIG. 3B, the frangible lower portion 64 is made from a 0.001" hard-temper foil that is resistant to stretching and a C11158 heat sealing coating that allow for lower sealing temperatures and shorter dwell times when sealed to PVC. A vinyl primer may be used to promote adhesion of the heat seal coating to the hard temper foil.

As shown, the blister pack 24 includes a plurality of deformable valve sites 56 that are operatively associated with respective valves 76 defined along the fluidic backbone 26. Each deformable valve site 56 is made from a flexible or deformable material that can be mechanically actuated by the reader 14 through valve cutouts 72 formed in the adhesive film 32. This mechanical actuation by the reader 14 changes the state of the valve 76 between open and closed positions in order to prevent or permit fluid flow communication. In addition, the blister pack 24 defines a pair of normally closed valve sites 58A and 58B that are in selective fluid flow communication with both ends of a dog bone channel 60. These normally closed valve sites 58A and 58B are operatively associated with respective valves 77A and 77B (FIG. 5) for preventing fluid flow communication across the dog bone channel 60 unless mechanically actuated by the reader 14 to an open position. To place the normally closed valves 77A and 77B in the open position, a puncture piston 142 similar to the one illustrated in FIG. 23 must be used to puncture through the normally closed valve sites 58A and 58B such that the valve sites 58d and 58B engage respective valves 77A and 77B to permit sample to flow through valves 77A and 77B by flowing across dog bone channel 60.

In one aspect, the method for manufacturing the blister pack 24 may include heat and pressure sealing particular areas of upper portion 62 against the frangible lower portion 64. For example, selective application of heat and pressure to these materials outside the areas of the blister pack 24 around the blister domes 38, finger channels 40, puncture valve sites 42, dog bone channel 60, normally closed valve sites 58A and 58B, and valve sites 56. This process allows portions of the cold formed and deformable upper portion 62 to be joined to the frangible lower portion 64; thereby defining the areas of the blister domes 38, finger channels 40, dog bone channel 60, normally closed valve sites 58A and 58B, and valve sites 56 to store liquids or establish fluid pathways for the flow of liquid reagents and the sample. In the alternative, only the blister domes 38 are manufactured using a heat or pressure sealing process, while the other topical features (e.g. finger channel (60), valve sites 56) may be formed using other processes for areas of the upper portion 62 to remain unbonded from the frangible lower portion 64.

In another aspect, the blister domes 38, finger channels 40, puncture valve sites 42, dog bone channel 60, normally closed valves 58A and 58B, and valve sites 56 may be cold formed and the cold formed material may be sealed against the frangible lower portion 64 after the addition of liquids to the blister domes 38 when fabricating the blister pack 24. Preferably, the blister pack 24 should also provide deep draw capabilities; an excellent light, oxygen, and moisture barrier; and resist delamination.

As further shown in FIG. 3, the blister domes 38 may be grouped such that particular blister domes 38 provide different reagents for performing a particular assay protocol. In one embodiment, each blister dome 38A may contain different reagents for use in a particular assay protocol, while blister domes 38B and 38C will contain reagents for performing other types of respective assay protocols. In this arrangement, each grouping of blister domes 38 is dedicated to provide particular reagents to a specific flow cell 94, 96 and 98 (FIG. 5), although certain blister domes 38 may contain the same reagent.

Figure 22:
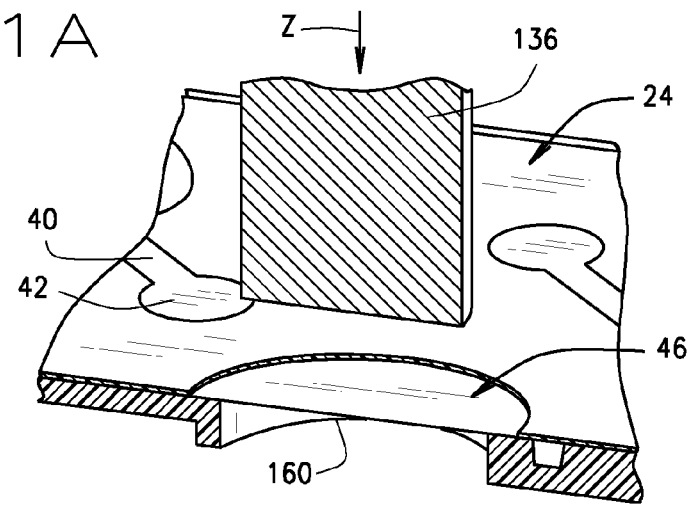
FIG. 22 is a cross-sectional view showing another piston of the reader actuating the sample reservoir for the controlled release of the sample.

Referring to FIG. 5-8, the fluidic backbone 24 provides the various fluidic pathways, fluid control components, storage areas, and controlled release functions for the cartridge 12. In one embodiment, the fluidic backbone 26 many be made from a cyclic olefin, such as Topas® 8007S-04 that is injection molding grade with a high moisture barrier capability, although other suitable plastic materials are contemplated. The fluidic backbone 26 includes a body 37 having an input port 44 in selective fluid flow communication with a sample reservoir through a valve 76A disposed along input channel 106. As shown in FIG. 22, the flexible adhesive film 32 covers the aperture 57 of the fluidic backbone 24 to collectively define a well 160 adapted to store and then positively displace the sample in a controlled manner from the well 160 when actuated by the reader 14. In one embodiment, the adhesive film 32 is made from a flexible film, such as an Arcare™ 8890 clear polyester film. This adhesive film 32 may be made from a clear, thin and flexible plastic film coated on both sides with a medical-grade, pressure-sensitive adhesive that is sufficiently compliant in nature such that liquid that enters and fills the well 160 stretches the adhesive film 32 outwardly. In this filled state, the reader 14 can mechanically actuate the sample reservoir 46 by pressing against the flexible adhesive film 32 to positively displace the sample from the sample reservoir 46.

The fluidic backbone 26 further includes a first waste chamber 80, second waste chamber 82 and third waste chamber 84 for the storage of waste products resulting from the electrochemical analysis performed by the cartridge 12. To permit venting of air from the sample reservoir 46, the third waste chamber 84 communicates with atmosphere through a vent 86 defined by body 37. In addition, the plurality of cross-shaped support bases 78 are defined along the surface of the first, second, and third waste chambers 80, 82 and 84 with each support base 78 providing structural support to a respective blister dome 38 of blister pack 24 when the cartridge 12 is assembled as noted above.

As shown, the sample reservoir 46 communicates with a vent channel 108 that permits evacuation of air to the third waste chamber 84 that is present in the input channel 106 and the sample reservoir 46 prior to the sample entering the input port 44. When the sample enters the input port 44, the sample forces the air present in the sample input channel 106 and sample reservoir 46 into the vent channel 108 for evacuation through vent 86. In this initial state prior to transferring the sample from sample transfer device 15 to the cartridge 12 shown in FIG. 9, valves 76A and 76B are in the open position, while normally closed valve 77A is in the closed position. This arrangement of open and closed valves isolates the sample reservoir 46 when the sample enters the input port 44 and allows the air present in the sample reservoir 46 to be expelled to the waste chamber 84.

Referring back to FIG. 5, the fluidic backbone 26 defines a first flow cell 94, second flow cell 96, and third flow cell 98, that are in selective fluid flow communication with each other through valves 76C, 76D and 76E. Valves 76C, 76D and 76E may be mechanically actuated by the reader 14 between a closed position to isolate the flow cells 94, 96 and 98 during performance of the assay protocols and an open position that permits sequential fluid flow communication when a sample is initially flows through each of the flow cells 94, 96 and 98 from the sample reservoir 46. As shown, flow cells 94, 96 and 98 each include a respective flow cell channel 94A, 96A and 98A adapted to receive fluid flow from the sample reservoir 46 and liquid reagents from the blister domes 38. The flow cell channels 94A, 96A and 98A are operatively associated with a respective sensor 28 for detecting electrochemical reactions and collecting data on the performance of the assay protocols.

Figure 30:
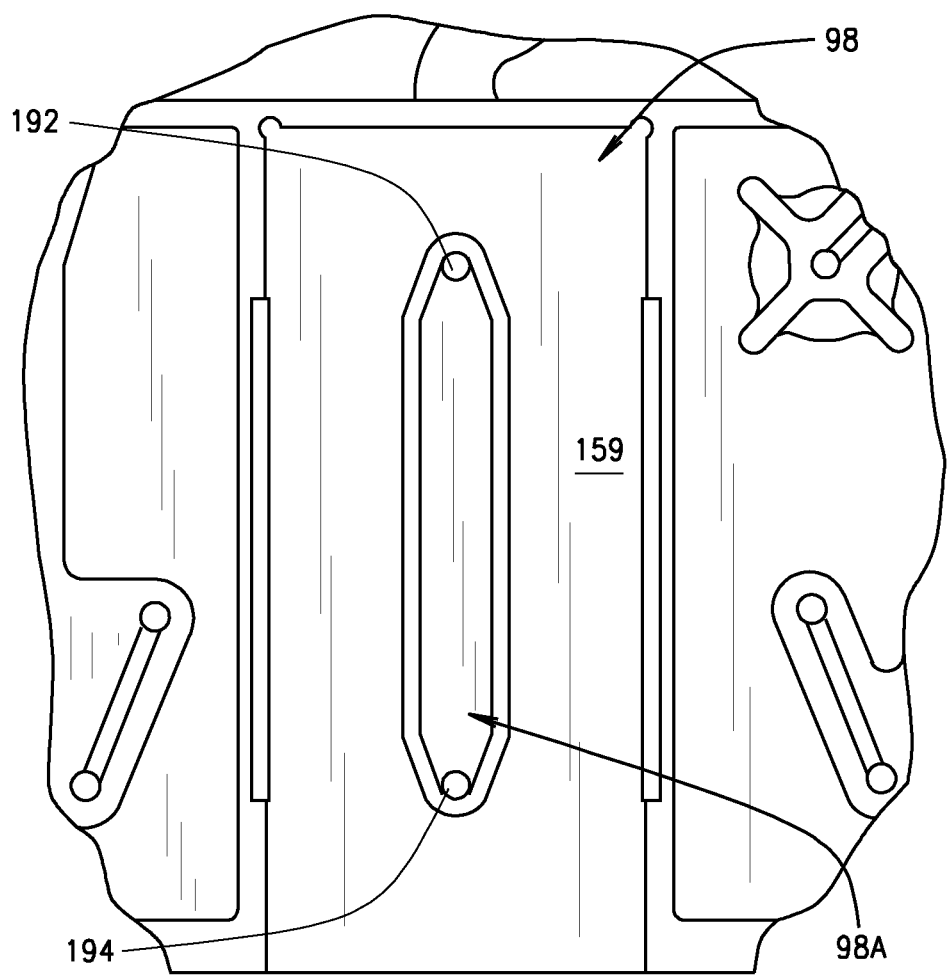
FIG. 30 is a plan view of the flow cell defined by the fluidic backbone.
Figure 31:
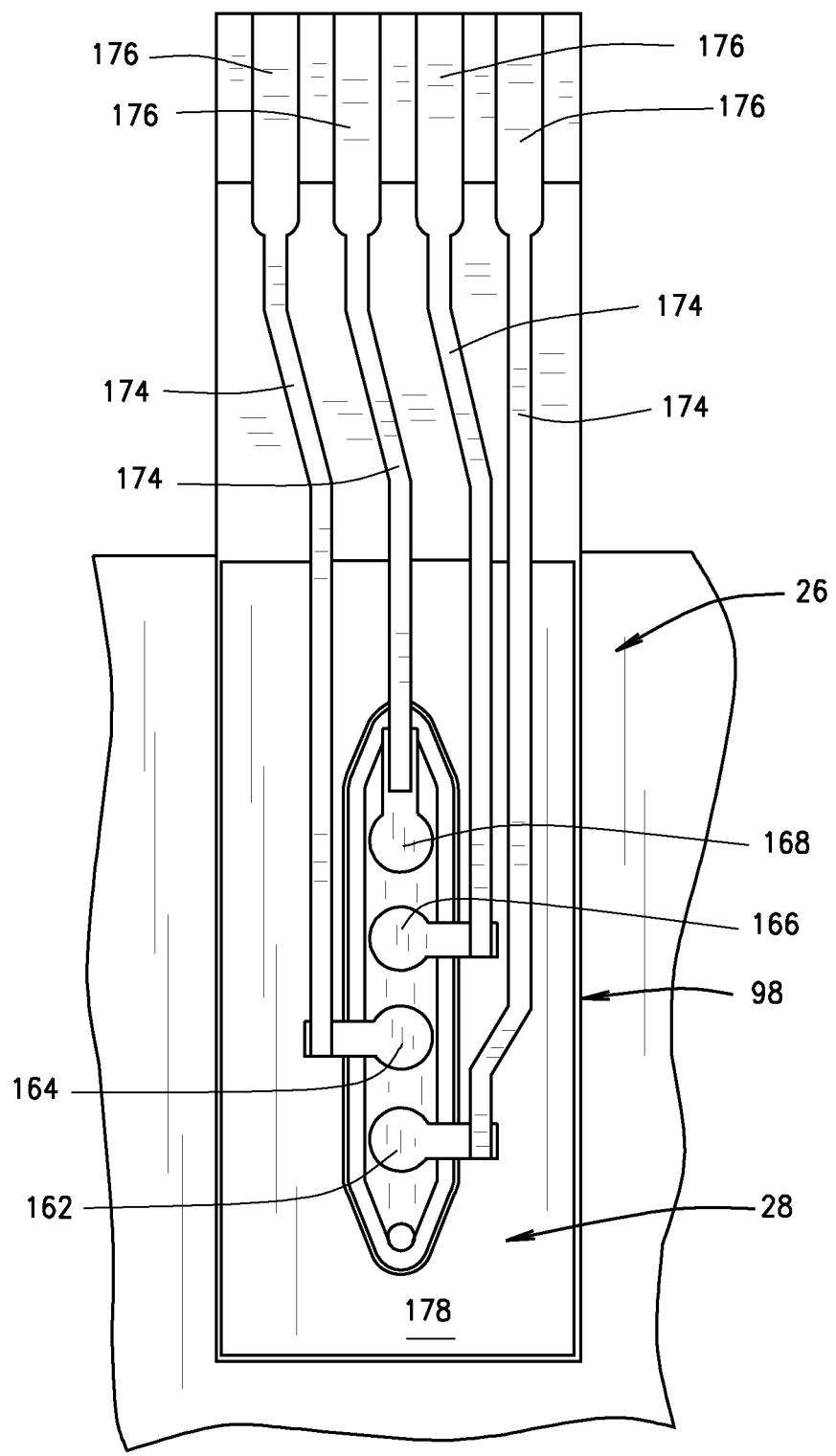
FIG. 31 is a plan view of the sensor operatively engaged to the flow cell.

For purposes of illustrating the structural and operational details of flow cells 94, 96 and 98, reference will be made solely to flow cell 98. Referring to FIGS. 30 and 31, flow cell 98 includes a flow cell well 159 that has a flow cell chamber 98A. The flow cell chamber 98A is the operative area where the electrochemical analysis is performed inside the cartridge 12. The flow cell chamber 98A is operatively associated with sensor 28 having electrodes 162, 164, 166 and 168 aligned along the length of chamber 98A. As further shown, the flow cell chamber 98A includes an inlet 192 that permits the ingress of fluid into the flow cell chamber 98A and an outlet 194 for allowing the egress of fluid from the flow cell chamber 98A.

Figure 5:
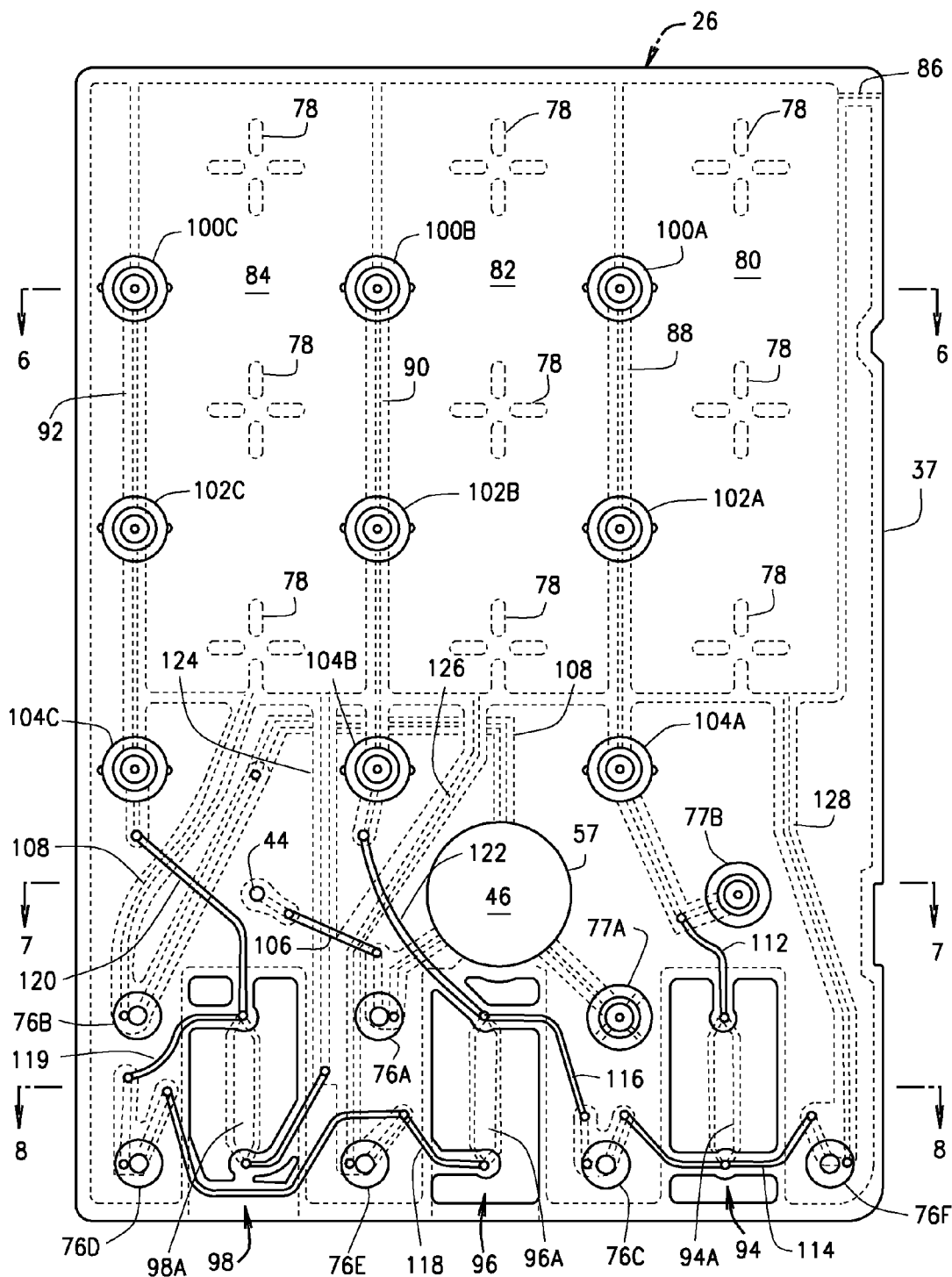
FIG. 5 is a schematic view of the fluidic backbone.
Figure 5A:
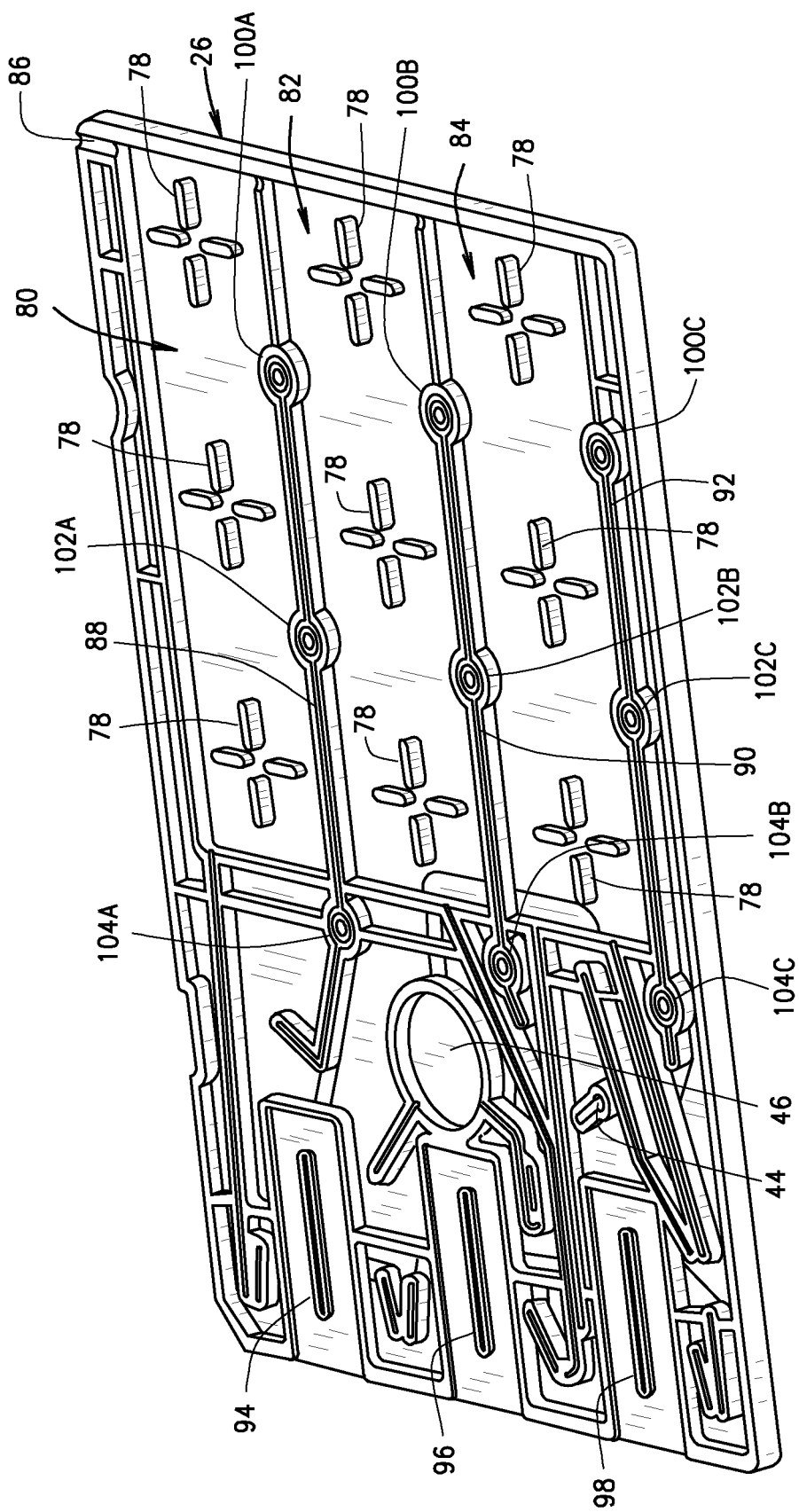
FIG. 5A is a perspective rear view of the fluidic backbone shown in FIG. 5 illustrating the structural aspects of the fluidic backbone.
Figure 20:
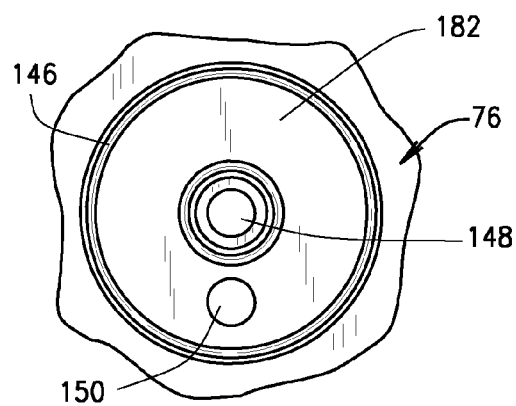
FIG. 20 is a top view of a valve used to control fluid flow through the cartridge.

Referring to FIG. 5, the disposal of waste products will be described in greater detail. The first flow cell 94 is operatively associated with a valve 76F that is in selective fluid flow communication with a waste channel 128 for permitting waste products from the first flow cell 94 to be evacuated into first waste chamber 80. Similarly, valve 76E is in selective fluid flow communication with a waste channel 126 such that, when valve 76E is in the open position, waste products from the second flow cell 96 may evacuated into the second waste chamber 82. Finally, the third flow cell 98 is in fluid flow communication with a waste channel 124 for allowing waste products from the third flow cell 98 to be evacuated into the third waste chamber 84.

Referring to FIGS. 3 and 5, the fluidic backbone 26 defines a first main channel 88, second main channel 90 and third main channel 92 for providing a fluid pathway to the flow cells 94, 96 and 98 from liquids that are stored and released in respective blister domes 38. In one embodiment, the first main channel 88 is in selective fluid flow communication with puncture valve sites 42 (FIG. 3), corresponding to puncture valve site bases 100A, 102A and 104A (FIG. 5), and communicates with the first flow cell 94 through inflow channel 112. Similarly, second main channel 90 is in selective fluid flow communication with puncture valve sites 42, corresponding to puncture valve site bases 100B, 102B and 104B, and communicates with second flow cell 96 through inflow channel 122, while the third main channel 92 is in selective fluid flow communication with puncture valve sites 42, corresponding to puncture valve site bases 100C, 102C and 104C, and communicates with third flow cell 98 through inflow channel 120.

As noted above, the main channels 88, 90 and 92 provide the fluid pathways for the flow of fluids to the respective flow cells 94, 96 and 98 that are released by the blister domes 38. In particular, blister domes 38A may provide the necessary liquid reagents through first main channel 88 for performing a specific assay protocol within the first flow cell 94, while blister domes 38B may provide the necessary liquid reagents through second main channel 90 for performing a specific assay protocol within the second flow cell 96. Similarly, blister domes 38C may provide the necessary liquid reagents through the third main channel 92 to perform a specific assay protocol in the third flow cell 98. In the alternative, air may be supplied in one more blister domes 38 rather than liquids. It is contemplated that the controlled release of fluids from the blister domes 38 will generate a bolus of air in front of the released fluid that will expel and evacuate any downstream fluid into the respective waste chambers 80, 82 and 84.

Referring to FIGS. 25, 27, and 31, a sensor 28 may be operatively engaged to each of the flow cells 94, 96 and 98 in order to detect the reactions created by performance of an assay protocol. In one embodiment, the sensor 28 may have a four-electrode arrangement that consists of a working electrode 162, first and second working calibration electrodes 164 and 166, and a reference electrode 168. The electrodes 162, 164, 166 and 168 are engaged to conductive portions 174 that a conductively connected to a respective contact 176 for operative engagement with the reader 14 for providing the signals from detected by sensor 28 to the software component 19 for processing of data.

In one aspect, the sensors 28 are constructed using a three-step process. In the first step, four layers are screen printed onto a flexible sheet of insulating plastic backing 180. The first layer that is screen printed comprises electrically conductive silver tracks followed by a second layer of a silver/silver chloride reference electrode 168. In addition, a layer consisting of a carbon working electrode is screen printed over a portion of each conductive silver track, and then a final layer of a dielectric insulating layer 178 is applied over the areas of the plastic backing 180 other than those areas of the plastic backing 180 containing working electrodes 162, 164 and 166. The dielectric layer 178 also covers the conductive portions 174, for example silver or other conductive material, to prevent any liquids from coming into contact with the conductive portions 174 during immersion in solutions or during the performance of a particular assay protocol. The result is a printed sheet that contains a plurality of sensors 28 in which rows of sensors 28 are cut out from the printed sheet for the second step of the process.

The second step involves a polymerization process wherein the screen printed sensors 28 are secured in a lid (not shown) of a bespoke electrochemical cell. Each row of sensors 28 has an exposed electrically conductive silver bar across the top of the row of sensors 28 to which each of the conductive portions 174 of the working electrodes 162, 164 and 166 are electrically connected. When the rows of sensors 28 are secured in the cell lid, an electrical connection between the cell and the conductive portions 174 is established. The bottom half of the cell contains a series of wells (not shown) to hold the polymerization solution and also the counter-electrodes required for the electrochemical polymerization process. The polymerization solution may contain a pyrrole monomer and a counterion.

A polymerization solution is placed into the wells of the electrochemical cell and the lid (with the row of sensors 28) is placed onto the cell. The working electrodes 162, 164 and 166 are fully immersed in the polymerization solution. A computer-controlled galvanostat is used to apply a series of current steps that drives current between the working electrodes 162, 164 and 166 of the sensor 28 (anode) and the counter-electrode in the cell (cathode). This results in a polypyrrole conductive film forming on the working electrodes 162, 164, and 166 of each sensor 28. Once the polymerization process has taken place, the rows of sensors 28 are removed from the lid of the cell and soaked in a high purity water, for example Milli-Q, to remove any residual counter-ions or unreacted monomer. After soaking, the rows of sensors 28 are placed in an incubator and allowed to dry for a predetermined period of time, for example overnight.

In the third step, the rows of polymerized sensors 28 are placed on to bespoke manufactured racks that control the orientation of the rows. The rack filled with rows of sensors 28 is placed onto the table of a bio-reagent dispensing system (not shown). The bio-reagent dispensing system will dispense the appropriate bio-reagents for the assay onto the polymerized working electrodes 162, 164 and 166 of each sensor 28. After all of the sensors 28 on a rack have been coated with the bio-reagent, the rack is removed from the bio-reagent dispensing system and placed in an incubator (not shown) to dry. For some bio-reagents, after drying the rows of sensors 28 are immersed in a stabilizer coating solution to preserve the activity of the bio-reagents. When the bio-reagents and any additional coatings are dry, the rows of sensors 28 are cut into the final shape of sensor 28 for use. During this step of the process, the conductive bar used during the polymerization process is removed and the electrical contacts 174 on the sensor 28 are trimmed flush to allow correct engagement with the reader 14 when the cartridge 12 is inserted into either docking station 52 or 54.

In the alternative, as shown in FIG. 26 the sensor 28A may include three working electrodes 162, 170, and 172 and a reference electrode 168 which are associated with a respective conductive portion 174 and have a similar configuration as the embodiment of sensor 28. However, the working electrodes 162, 170 and 172 are operative in a manner that the detected results from each electrode 162, 170 and 172 are averaged by the software component 19 to reduce the coefficient of variance in the final result.

To accommodate lot-to-lot variations during assay manufacturing, a bar code (not shown) may be placed on the cartridge 12 during manufacturing that may be detected by the reader 14 when the cartridge 12 is engaged to one of the docking stations 52 or 54. The reader 14 will use the data from the bar code to adjust the calibration previously stored in the software component 19. However, an encoded calibration curve for the cartridge 12 must remain valid for the entire shelf life of that assay lot. There are two major areas that need to be addressed. First the substrate liquid may oxidize over time and the enzyme/antibody conjugate activity may decay by various pathways over time. Most of the mainstream immunoassay analyzers compensate for this decay by requiring a user to re-calibrate each lot at set intervals, typically every 30 days, despite the fact that the overall shelf life of the assay may be 12 months. This re-calibration is performed using lyophilized samples supplied with a kit (not shown) provided to the user. However, this re-calibration approach for the cartridge 12 of the electrochemical detection system 10 would be unacceptable since the need for frequent re-calibration can be interpreted as a complex activity.

In order to circumvent this re-calibration issue, a new approach is disclosed for the electrochemical detection system 10 that does not require any user activity because the shelf life adjustment is made at the same time the actual assay protocol is performed. In one embodiment, a three-electrode sensor 28 (not shown) may be used to accomplish this goal. The first electrode acts as the standard reference electrode, the second electrode acts as the standard sample (e.g. target detection) electrode, and the third electrode may be identical to the second electrode except that the third electrode may be coated with streptavidin that has a fixed biotyinylated quantity of the analyte in question that is already bound. No more target analyte may bind to the third electrode even though such an analyte is present in the sample.

When the sample and reagents are added to all of the electrodes, the reference electrode will see the same assay conditions as the detection electrode. Any deterioration in the reagents would be detected by the third electrode, as compared to the measurement made at the time of manufacture, and this change in signal may be used to correct the sample electrode result (e.g. second electrode) by applying both an offset and a scaling factor of the form y=mx+c, where c is the intercept and m is the slope. An adjustment to the sample result may be performed in the software component 19. For example, a 10% loss in enzyme activity over time would be returned as a 10% lower value compared to that encoded for the third electrode at initial testing and thus the resulted returned by the detection electrode would be adjusted by a +10%. The advantage of this procedure is that every test is effectively verified and variances such as stability, temperature or flow can be compensated for, within certain limits, without resorting to complex engineering solutions. In theory, the final assay % cv should be reduced.

Referring to FIGS. 9-19 the sequence of operation of the cartridge 12 as well as the various flow of fluids through the fluid pathways and channels of the cartridge 12 are illustrated. As shown in FIG. 9, prior to engagement with the reader 14 a sample, such as whole blood, may be transferred from the sample transfer device 15 (FIG. 28) to the cartridge 12 by engaging the device 15 to the input port 44 and injecting the sample into the inflow channel 106. In one embodiment, the sample reservoir 46 may have a maximum storage capacity of 250 μL for storing the sample, although other maximum storage capacities are contemplated. As noted above, in its initial state prior to engagement with reader 14, the valves 76A and 76B in communication with two sample reservoir 46 are in the open position to permit fluid flow communication which is represented by flow pathway A, while normally closed valves 77A and 77B are in their normally closed position in order to isolate the sample reservoir 46 from the flow cells 94, 96 and 98. Flow pathway A shows that the sample flows from the input port 44 to the sample reservoir 46 and through the vent channel 108 until the air present in the sample reservoir 46 is fully expelled into the third waste chamber 84. In this initial state, valves 76C, 76D, 76E and 76F are in the initially open position, although normally closed valves 77A and 77B are in the closed position.

Figure 23:
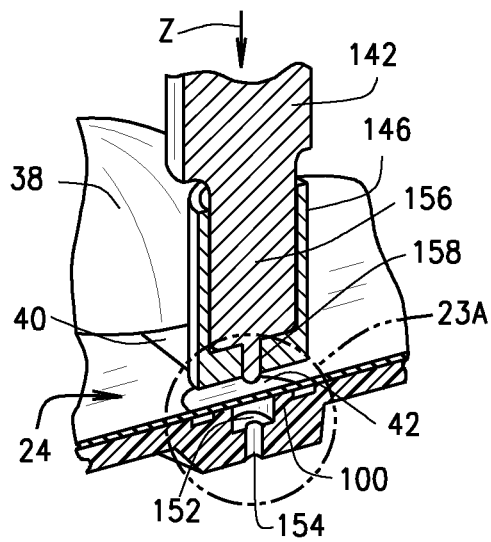
FIG. 23 is a cross-sectional view showing a puncture piston of the reader engaging the puncture valve site of the blister pack and puncture site base of the fluidic backbone prior to the controlled release of liquid into the fluidic backbone.
Figure 23A:
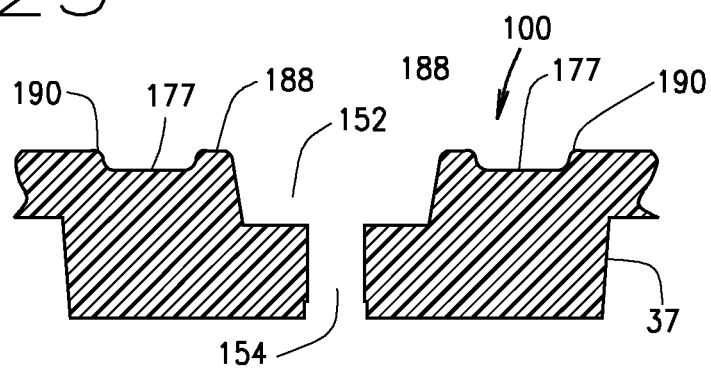
FIG. 23A is an enlarged cross-sectional view of the fluidic backbone taken from FIG. 23 showing the puncture site base.

Referring to FIG. 23, the arrangement of the normally closed valves 77A, 77B and channel valve sites 58 are similar in structure and operation as the arrangement of the puncture valve sites 42 and puncture site bases 100 in that the channel valve sites 58 are operable to prevent fluid flow communication through the valves 77A and 77B until mechanically actuated by the reader 14. To actuate normally closed valves 77A and 77B, a puncture piston 142 defining a spike portion 156 having a distal spike 158 and fitted with all elastomeric boot 146 moves downwardly along the Z direction to engage and deform the upper portion 62 while the frangible lower portion 64 breaks apart, thereby establishing fluid flow communication across the dog bone channel 60 as liquid flows between normally closed valves 77A and 77B. In addition, the puncture piston 142 may reengage the channel valve sites 58 such that the application of force by the elastomeric boot 146 against the normally closed valves 77A and 77B forces the channel valves sites 58 against the inner and outer raised rims 188 and 190 that seals the outlet 154 of valves 77A and 77B, thereby preventing fluid flow communication across the dog bone channel 60.

As shown in FIG. 10, once the sample is transferred to the cartridge 12 and fills the sample reservoir 46 and vent channel 108, the cartridge is engaged to the reader 14 at either docking port 52 or 54 such that the reader 14 places the valves 76A and 76B in the closed position. In the closed position, the sample reservoir 46 becomes isolated from the input port 44 and waste chamber 84. In addition, valves 76C, 76D, 76E and 76F remain in the initially open position.

Figure 21:
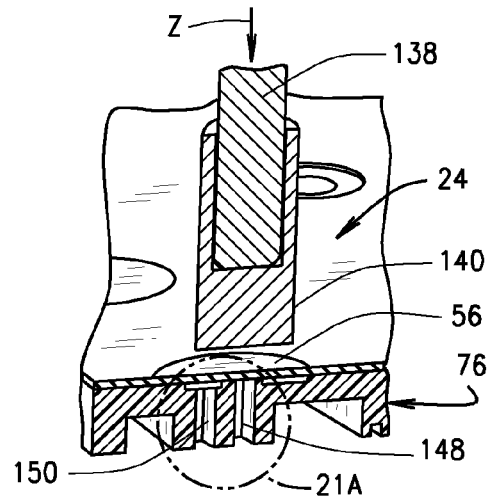
FIG. 21 is a cross-sectional view showing a piston of the reader actuating one of the valves of the cartridge.
Figure 21A:
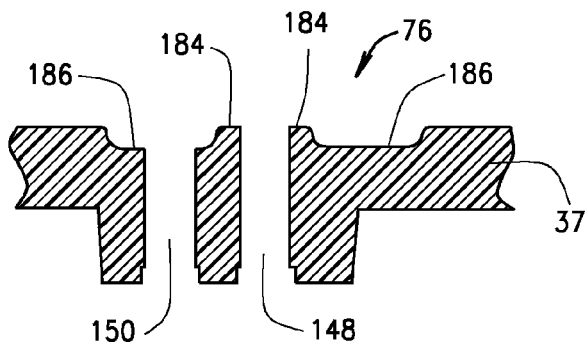
FIG. 21A is an enlarged cross-sectional view of the fluidic backbone taken from FIG. 21 showing the valve.

Referring to FIGS. 21 and 21A, the mechanical actuation of the valves 76 by the reader 14 is shown. As noted above, the valve 76 is in operative association with valve site 56 such that the valve piston 138 of the reader 14 may mechanically actuate the valve 76 by engaging and disengaging the valve site 56. In one embodiment, the valve 76 may include a recess 186 that defines a chamber 182 surrounded by a cup portion 146. The recess 188 is in selective fluid flow communication with an inlet 148, for the ingress of fluid into the recess 186 and an outlet 150 for the egress of fluid from the recess 186. As further shown, a raised inner rim 184 is defined around the inlet 148 such that the inlet 148 has a more raised profile than the outlet 150 which allows the valve 76 to be seal and unsealed by the valve site 56. The valve 76 may be placed in the closed position when the valve piston 138 engages the valve site 56 such that the valve site 56 presses against the raised inner rim 184 that seals the inlet 148 and prevents fluid flow communication between the inlet 148 and the outlet 150. Conversely, the valve 76 may be placed in the open position by disengaging the valve piston 138 from the valve site 56 to disengage the valve site 56 from the inner rim 188 in order to establish fluid flow communication between the inlet 148 and outlet 150. In addition, the valve piston 138 is provided with an elastomeric boot 140 that deforms and flattens out upon direct contact with the valve site 56. This contacting action causes the elastomeric boot 140 to conform to the raised inner rim 184, thereby establishing sufficient contact between the valve site 56 and valve 76 to seal the inlet 148. In one embodiment, the elastomeric boot 140 may be made from a flexible material, such as silicone or rubber.

Referring to FIG. 11, once the valves 76A and 76B are placed in the closed position, the normally closed valves 77A and 77B opened to permit fluid flow communication through dog bone channel 60 as discussed above. In addition, valves 76E and 76F are placed in the closed position to isolate the flow cells 94, 96 and 98 from waste channels 124, 126 and 128, respectively.

As shown in FIG. 12, the flow of sample is initiated by crushing or deforming the sample reservoir 46 by the reader 14 to force the sample across the dog bone channel 60 (FIG. 3) and into the first flow cell 94 by flowing through inflow channel 112 as illustrated by flow pathway B. The positions of the valves 76A-76F remains the same during the entire duration of flow pathway B as the sample sequentially flows through the second and third flow cells 96 and 98.

Referring to FIG. 22, the sample reservoir 46 is deformed by engagement of the reservoir piston 136 against the flexible material (e.g. adhesive film 32) of the sample reservoir 46 in the Z direction, thereby positively displacing the sample from the well 160 and towards the dog bone channel 60. The rate of flow of the sample through the cartridge 12 from the sample reservoir 46 can be modified by changing the force applied by the reservoir piston 136 including the rate of travel of the reservoir piston 136 along the Z direction. In one embodiment, the reservoir piston 136 may have a generally circular configuration, although other suitable configurations of piston 136 are contemplated, such as square, rectangular, oval, etc that comport with the configuration of the sample reservoir 46.

Once the sample travels through the first flow cell 94, the sample enters the second flow cell 96 by traveling through fluidic channels 114 and 116 as illustrated in FIG. 13. Referring to FIG. 14, the sample then flows through fluidic channel 118 until the sample reaches the third flow cell 98 as shown by flow pathway B. After the sample has sequentially flowed through the first, second and third flow cells 94, 96 and 98, the sensor 28 located at the first flow cell 94 will be exposed to the most volume of sample, while sensors 28 located at the second and third flow cells 96 and 98 will be exposed to less volume of sample due to their relative downstream positions. For example, the sensor 28 at the first flow cell 94 may be exposed to 168 µl, while the sensor 28 at the second flow cell 96 may be exposed to 146 µl and the sensor 28 at the third flow cell 98 exposed to 120 µl.

Once the flow of sample through the first, second and third flow cells 94, 96 and 98 is completed, the first, second and third flow cells 94, 96, and 98 are isolated from one another by closing valves 76C and 76D as well as valves 77A and 77B as shown in FIG. 15. In addition, valves 76E and 76F are placed in the open position by the reader 14 in order to establish fluid flow communication from the first, second and third flow cells 94, 96 and 98 with respective first, second and third waste chambers 80, 82 and 84. In this stage, residual sample may remain in portions of the fluidic channels 116, 118, and 119. Valves 76A and 76B remain in the closed position.

Referring to FIG. 16, the liquid reagent (e.g., conjugate) may now be released after the first, second and third flow cells 94, 96 and 98 have been isolated by two step mechanical actuation of the puncture sites 46 and blister domes 38 by the reader 14. For example, puncture site bases 10A, 100B and 100C are placed in the open position after mechanical actuation of those puncture valve sites 100 by the reader 14 shown in FIG. 23 to establish fluid flow communication between the puncture site bases 100A, 100B and 100C and respective first, second and third main channels 88, 90 and 92. Once the puncture site bases 100A, 100B and 100C are in the open position when the frangible lower portion is caused to break apart by the reader 14 liquid reagent (conjugate) may begin to flow from the respective puncture valve sites 100A, 100B and 100C as the blister domes 38A, 38B and 38C are deferred by piston 132 such that, the liquid reagent (conjugate) enters a respective main channel 88, 90 and 92 (FIG. 5) for eventual entry into a respective flow cell 94, 96 and 98 as denoted by flow pathway C. The movement of liquid reagent (conjugate) through the main channels 88, 90 and 92 forces a bolus of air into those channels 88, 90 and 92 through the first, second and third flow cells 94, 96 and 98 in order to expel the sample as illustrated by flow pathway D, E and F, respectively. Subsequent release of other liquids will generate the same bolus of air to expel any downstream fluids.

Referring to FIG. 17, as noted above once the liquid reagent (conjugate) begins to flow down main channels 88, 90 and 92, soon after the puncture valve sites 42 are opened the reader 14 mechanically actuates the deformable blisters 38A, 38B and 38C (FIG. 3) to positively displace the liquid reagent into the first, second and third flow cells 94, 96 and 98 in the manner shown in FIG. 24. As illustrated, the dome piston 132 applies a force against the blister domes 38A, 38B, and 38C such that the volume of chamber 130 for each blister dome 38 is decreased. This forces the liquid reagent (conjugate) to flow through a respective finger channel 40 and enter one of the main channels 88, 90 and 92 through puncture site bases 100A, 100B and 100C. As this point, the sample has been evacuated from the flow cells 94, 96 and 98 through waste channels 124, 126 and 128 and into the first, second and third waste chambers 80, 82 and 84, respectively. The first, second and third flow cells 94, 96 and 98 remain isolated from one another as multiple fluids are allowed to flow through each flow cell 94, 96 and 98.

Referring to FIG. 18, the liquid wash may then be released by actuating the puncture site bases 102A, 102B and 102C and then mechanically actuating the blister domes 38 that contain the liquid wash in the same manner as the liquid (conjugate) described in association with FIGS. 23 and 24. Flow pathway G illustrates the flow of liquid wash through the first, second and third flow cells 94, 96 and 98 and into the waste channels 124, 126 and 128. In the alternative, the blister domes 38 may contain air rather than wash or substrate liquids used for the wash function.

As shown in FIG. 19, the liquid substrate is then released by actuating puncture site bases 104A, 104B and 104C and forced through the respective first, second and third flow cells 94, 96 and 98 as illustrated by flow pathway G. The liquid substrate forces the liquid wash from the first, second and third flow cells 94, 96 and 98 and into the waste chambers 80, 82 and 84 so that the sensors 28 may detect the liquid substrate. After an appropriate duration, the flow of liquid substrate is terminated and the potential is generated by the assay reaction across an embodiment having a working electrode 162 and the reference electrode 168 and the signals from these electrodes 162 and 168 are sent to the software component 19 for processing of the data.

In one aspect, the electrochemical detection system 10 includes the capability of performing rapid immunoassay reactions within cartridge 12 by utilizing the sequentially controlled release of fluids through the flow cell chambers 94A, 96A and 98A when the assay protocols are conducted. It is known that the rate of chemical reaction to within reaction range of the second molecule followed by the likelihood that the reaction will occur. Higher concentrations of these molecules in the same vicinity will result in faster reaction rates occurring.

In a typical immunoassay of the prior art, reagents may be consecutively pipetted into a microtiter tray cuvette that contains antibodies attached to the surface of the cuvette. The target analyte binds to the antibody in a chemical reaction. In this format, it can take 30-40 minutes for the chemical reactions to occur in order to obtain a result for detection. In the microtiter tray format in particular, antibodies attached to the surface of the cuvette must react with the target analyte molecules.

As target molecules closest to the antibodies bind/react with the antibodies the region closest to the antibodies inevitably gets depleted of target molecules. Diffusion of new target molecules to this area must occur in order to replenish the area and permit further binding to occur. However, this type of diffusion limited reaction-type system is slow and requires more time for such binding reactions to occur. Similarly, as other reagents are added that also require interaction with the antibodies the rate of diffusion in the bulk solution will control the rate of the reactions that may occur. One method is to agitate the bulk solution in the cuvette by using a stirring bar or by agitating the actual microtiter tray. This agitating action refreshes the region closest to the antibodies that provides new target molecules.

Microfluidic platforms, such as disposable cartridges, can only store small volumes of fluid in comparison to the microtiter tray format that has a larger storage capacity, however, rapid immunoassay reactions are still achievable using flow cells 94, 96 and 98. The flow cell format of cartridge 12 allows the surface area closest to the antibodies to be replenished by sequentially flowing liquids, such as reagents, through flow cells 94, 96 and 98, thereby achieving the agitation effect noted above. In the alternative, cartridge 12 may have the capability of flowing a small block of liquid, such as reagent, in a back and forth motion over the surface closest to the antibodies. This alternative arrangement provides the same replenishing action using less reagent and sample. As such, both arrangements rapidly redistribute the target analyte and reagents evenly throughout the solution, thereby preventing the reactions from becoming diffusion limited.

In one embodiment, the cartridge 12 may have a plasma separation component (not shown) that utilizes a glass fiber filter to extract plasma from the whole blood sample after entry of the sample through the input port 42 such that plasma is stored in the sample reservoir 46. The extraction of plasma from the whole blood may be accomplished by allowing the blood to wick or filter through the body of the glass fiber filter for a predetermined amount of time before a working fluid, such as saime, is used to flush the plasma from the glass fiber filter. In the alternative, the plasma separation component may be a part of the sample transfer device 15 shown in FIG. 28. The sample transfer device 15 may be designed to interface with a conventional vacutainer for obtaining a whole blood sample for testing in the cartridge 12 which then may be engaged to the input port 42.

In one aspect discussed above, the electrochemical detection system 10 may perform a plurality of assay protocols simultaneously. In one embodiment, a TSH protocol may be performed using one of the flow cells 94, 96 or 98. A stock calibrant may be diluted to provide a range of concentrations. A sample (e.g., 150 μL volume) is transferred from the sample reservoir 46 at a flow rate of 1 μL per second followed by the introduction of a conjugate (e.g., 150 μL volume) at the same flow rate. A PBS wash buffer (e.g., 400 μL volume) is then introduced at a flow rate of 3 μL per second. Once the wash buffer is added, a substrate (e.g., 200 μL volume) is introduced at a flow rate of 3 μL per second. Sensors 28 may then be read using an applied current of −115 mV for 10 seconds and then allowing an open circuit potential (OCP) for 90 seconds. The mV reading at the end of a 90 second OCP is taken as the final value by the software component 19. In the alternative, clear fitting analysis by the software component 19 may provide a better quality result by using all of the kinetic curve information available rather than simply an end point.

In another embodiment, the following assay reagents may be stored in the blister domes 38 for use in performing different assay protocols in cartridge 12:

Assay Reagents:
  TSH monoclonal antibody coated sensors at 50 μg/mL
  TSH monoclonal antibody
  TSH calibrant standard 3500 mIU/mL
  TSH conjugate buffer
  TSH sample diluent
  SigmaFAST OPD substrate reagent
  Goat anti mouse coated sensors at 50 μg/mL
  Goat anti mouse antibodies
  Anti T4 monoclonal antibody
  T4 tracer
  Phosphate Buffered Saline
  Stabilzyme HRP
  T4 serum sample Assay Protocol—TSH-Typical Sandwich Immunoassay The conjugate is first diluted at a ratio of 1:500 in TSH conjugate buffer and the calibrant is diluted in a TSH sample diluent to provide a concentration of 100, 10, 1, 0.1 and 0.01 mIU/mL. Sample was added using a volume of 150 µL and a flow rate of 1 µL per second. In one embodiment, the assay protocol may require that 150 µL of conjugate be added at a flow rate of 1 µL per second followed by 400 µL of wash buffer at a flow rate of 3 µL per second. Finally, 200 µL of substrate is added at a flow rate of 3 µL per second. For example, phosphate buffered saline may be used as the wash buffer, while SigmaFAST may be used as the substrate in a concentration of one set of SigmaFAST tablets for every 50 mL MilliQ water. The following flow times may be used: TSH sample=2.5 minutes, conjugate=2.5 minutes, wash buffer=2.25 minutes, substrate=1.25 minutes, read time=1 minute and 40 seconds. The assay protocol may be performed in less than 10 minutes.

The sensors 28 are then read using an applied voltage of −115 mV for 10 seconds and then allowing an open circuit potential (OCP) for 90 seconds. The mV reading at the end of the 90 second OCP was taken as the final value.

Assay Protocol—Free T4-Typical Competitive Immunoassay

The conjugate was diluted 1:5000 in Stabilzyme HRP and the T4 antibody diluted in a Phosphate Buffered Saline to provide a final concentration of 1.0 µg/mL. A sample having a T4 antibody in a ratio of 25 µL antibody to 100 µL sample is provided to one of the flow cells 94, 96 or 98 followed by the wash buffer and a substrate. For example, a phosphate buffered saline may be used as the wash buffer, while the substrate may be provided at a concentration of one set of SigmaFAST tablets added for every 50 mL of MilliQ water.

In one embodiment, the sample with the antibodies may have a volume of 150 µL and a flow rate of 1 µL per second when positively displaced by the sample reservoir 46 to one or more of the flow cells 94, 96 and 98. Once the sample is displaced, 150 µL of tracer is then provided at a flow rate of 1 µL per second followed by 400 µL of wash buffer at a flow rate of 3 µL per second. Finally, 200 µL of substrate is provided at a flow rate of 3 µL per second. The following flow times may be used: Free T4 sample=2.5 minutes, conjugate=2.5 minutes, wash buffer=2.25 minutes, substrate=1.25 minutes, read time=1 minute and 40 seconds. The assay protocol may be performed in less than 10 minutes.

The sensors 28 are then read using an applied voltage of −115 mV for 10 seconds and then allowing an open circuit potential (OCP) for 5 seconds, applying −115 mV for 8 seconds, allowing OCP for 8 seconds, re-applying −115 mV for 8 seconds and then allowing an OCP for 90 seconds. The mV reading at the end of the 90 second OCP is taken as the final value by the software component 19.

In another aspect of the electrochemical detection system, the reader 14 may only mechanically actuate the cartridge 12 from only one side of the cartridge 12. This permits the reader 14 to provide a heating source (not shown) for thermally controlling the side opposite of the side being mechanically actuated by the reader 14.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A cartridge for performing a plurality of assay protocols comprising:
    a blister pack including a plurality of blister domes for storing a respective reagent; the blister pack having a deformable upper portion and a frangible lower portion for the controlled release of the respective reagent when a mechanical force is applied to one or more of the plurality of blister domes;
    a fluidic backbone engaged to the blister pack, the fluidic backbone including a plurality of channels in selective fluid flow communication with a plurality of flow cells through an arrangement of valves such that each of the plurality of flow cells is isolated from the other flow cells during the performance of a plurality of assay protocols, the fluidic backbone defining at least one puncture site base, wherein the at least one puncture site base comprises a raised inner rim and a raised outer rim and defines an outlet and a well in fluid communication with at least one of the plurality of channels;
    a plurality of sensors operatively associated with a respective flow cell for detecting a reaction during the performance of a plurality of assays;
    wherein each of the plurality of sensors comprises at least one working electrode and a reference electrode supported by a backing;
    wherein the deformable upper portion and the frangible lower portion define a finger channel in fluid flow communication between one of the plurality of blister domes and at least one puncture valve site; and
    wherein the blister pack is engaged to the raised inner rim and the raised outer rim so that the at least one puncture site base is positioned immediately adjacent to the at least one puncture valve site.

2. The cartridge of claim 1, further including a flexible adhesive film engaged between the blister pack and the fluidic backbone.

3. The cartridge of claim 2, wherein a sample reservoir is formed between the flexible adhesive film and the fluidic backbone.

4. The cartridge of claim 3, wherein the sample reservoir deforms the flexible adhesive film when a liquid fills the space between the fluidic backbone and the flexible adhesive film.

5. The cartridge of claim 1, wherein the arrangement of valves includes a plurality of valve sites defined by the blister pack that correspond to a plurality of valves in communication with a respective channel defined by the fluidic backbone for collectively preventing or permitting fluid flow through the respective channel, wherein each of the plurality of valves defines an inlet in selective fluid flow communication with an outlet through a well, wherein each of the plurality of valve sites includes a deformable material adapted to engage the valve to prevent fluid flow communication between the inlet and the outlet and disengage from the valve to permit fluid flow communication between the inlet and the outlet.

6. The cartridge of claim 5, wherein the cartridge is adapted to operatively engage a reader such that the reader mechanically actuates one or more of the plurality of valve sites to prevent or permit fluid flow communication by engaging or disengaging the one or more of the valve sites relative to a respective one of the plurality of valves.

7. The cartridge of claim 1, wherein the cartridge is adapted to operatively engage a reader such that the reader mechanically actuates one or more of the plurality of blister domes such that the deformable upper portion becomes deformed while the frangible lower portion breaks apart.

8. The cartridge of claim 7, wherein each of the plurality of blister domes contains a fluid, and each of the plurality of blister domes is in fluid flow communication with a puncture valve site that corresponds to a puncture site base for establishing fluid flow communication with a channel when the puncture site base is mechanically actuated by the reader.

9. The cartridge of claim 8, wherein fluid from the plurality of blister domes is released into the respective channel by mechanically actuating the puncture valve site to establish fluid flow communication with the respective channel, and then mechanically actuating the plurality of blister domes such that liquid is released from the plurality of blister domes and through a respective puncture valve site, wherein mechanical actuation of the plurality of blister domes and the puncture valve sites causes the deformable upper portion to become deformed and the frangible lower portion to break apart in order to establish fluid flow communication between the plurality of blister domes and one of the plurality of channels upon mechanical actuation by the reader.

10. The cartridge of claim 1, wherein each of the plurality of sensors includes an arrangement of four electrodes that are operatively associated with a respective one of the plurality of flow cells for detecting an electrochemical reaction.

11. The cartridge of claim 10, wherein the arrangement of four electrodes includes three working electrodes and a reference electrode.

12. The cartridge of claim 11, wherein at least one of the working electrodes is a working calibration electrode for providing a means of calibrating each of the plurality of sensors.

13. The cartridge of claim 1, further including a bottom lid that is engaged to the fluidic backbone for defining the plurality of channels.

14. The cartridge of claim 1, wherein the fluid flow is initiated by mechanically engaging the puncture valve site against the puncture site base to establish fluid flow communication between one of the plurality of blister domes and the puncture site base, and then mechanically actuating the one of the plurality of blister domes to permit the release of liquid through the outlet of the puncture site base.

15. The cartridge of claim 1, wherein a fluidic pathway is defined between the deformable upper portion and the frangible lower portion such that the mechanical actuation of the blister pack causes the deformable upper portion to deform and the frangible lower portion to break apart.

16. A cartridge for performing a plurality of assay protocols comprising:
 a blister pack including a plurality of blister domes for storing a respective reagent; the blister pack having a deformable upper portion and a frangible lower portion for the controlled release of the respective reagent when a mechanical force is applied to one or more of the plurality of blister domes;
 a fluidic backbone engaged to the blister pack, the fluidic backbone including a plurality of channels in selective fluid flow communication with a plurality of flow cells through an arrangement of valves such that each of the plurality of flow cells is isolated from the other flow cells during the performance of a plurality of assay protocols;
 a plurality of sensors operatively associated with a respective flow cell for detecting a reaction during the performance of a plurality of assays;
 wherein the cartridge is adapted to operatively engage a reader capable of mechanically actuating the cartridge from only one side of the cartridge; and
 wherein the reader mechanically actuates the cartridge using a plurality of actuating pistons or rollers.

\* \* \* \* \*